US 7,432,093 B2

(12) United States Patent
Shi

(10) Patent No.: US 7,432,093 B2
(45) Date of Patent: Oct. 7, 2008

(54) SOLUBLE, FUNCTIONAL APOPTOTIC PROTEASE-ACTIVATING FACTOR 1 FRAGMENTS

(75) Inventor: Yigong Shi, Plainsboro, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 103 days.

(21) Appl. No.: 11/045,540

(22) Filed: Jan. 28, 2005

(65) Prior Publication Data

US 2006/0106200 A1 May 18, 2006

Related U.S. Application Data

(60) Provisional application No. 60/628,000, filed on Nov. 15, 2004.

(51) Int. Cl.
*C07K 14/00* (2006.01)
(52) U.S. Cl. .................. 435/183; 435/440; 530/350; 530/300
(58) Field of Classification Search ............ 530/350, 530/300; 435/183, 440
See application file for complete search history.

(56) References Cited

U.S. PATENT DOCUMENTS 6,403,765 B1 * 6/2002 Alnemri .................. 530/350

FOREIGN PATENT DOCUMENTS

WO    WO 9855615 A1 * 12/1998
WO    WO 0100827 A1 *  1/2001

OTHER PUBLICATIONS

Alnemri et al. "Truncated APAF-1 and methods of use," SEQ ID No. 1 alignment result 6, Database: Issued_Patents_AA, Jun. 16, 1998.*
Acehan et al., 2002, Mol. Cell 9:423-432.
Benedict, 2000, J. Biol. Chem. 275:8461-8468.
Cecconi et al., 1998, Cell 94:727-737.
Collaborative Computational Project, 1994, Acta Crystallogr. D50:760-763.
Dangl et al., 2001, Nature 411:826-833.
Danial et al., 2004, Cell 116:205-219.
Fearnhead et al., 1998, Proc. Natl. Acad. Sci. 95:13664-1366.
Gai et al., 2004, Cell 119:47-60.
Gai et al., 2004, J. Biol. Chem. 279:38952-38959.
Genini et al., 2000, J. Biol. Chem. 275:29-34.
Green et al., 2002, Cancer Cell 1:19-30.
Hanahan et al., 2000, Cell 100:57-70.
Holm et al., 1993, J. Mol. Biol. 233:123-138.
Horvitz, 2003, ChemBioChem 4:697-711.
Hu et al., 1998, J. Biol. Chem. 273:33489-33494.
Hu et al., 1999, EMBO J. 18:3586-3595.
Inohara et al., 1999, J. Biol. Chem. 274:14560-14567.
Inohara et al., 2001, Oncogene 20:6473-6481.
Jaroszewski et al., 2000, Proteins 39:197-203.
Jiang et al., 2000, J. Biol. Chem. 275:31199-31203.
Jones et al., 1991, Acta Crystallogr. A47:110-119.
Juliusson et al., 1996, J. Clin. Oncol. 14:2160-2166.
Kanuka et al., 1999, Mol. Cell 4:757-769.
Kaufmann et al., 1996, Mech. Dev. 57:3-20.
Kawasaki et al., 1993, Blood 81:597-601.
Lenzen et al., 1998, Cell 94:525-536.
Leoni et al., 1998, Proc. Natl. Acad. Sci. USA 95:9567-9571.
Li et al., 1997, Cell 91:479-489.
Lupas et al., 2002, Curr. Opin. Struct. Biol. 12:746-753.
Neuwald et al., 1999, Genome Res. 9:27-43.
Ogura et al., 2001, J. Biol. Chem. 276:4812-4818.
Otwinowski et al., 1997, Methods Enzymol. 276:307-326.
Poyet et al., 2001, J. Biol. Chem. 276:28309-28313.
Qin et al., 1999, Nature 399:549-557.
Riedl et al., 2004, Nature Rev. Mol. Cell. Biol. 5:897-907.
Rodriguez et al., 1999, Genes Dev. 13:3179-3184.
Rodriguez et al., 1999, Nat. Cell Biol. 1:272-279.
Saleh et al., 1999, J. Biol. Chem. 274:17941-17945.
Soengas et al., 1999, Science 284:156-159.
Soengas et al., 2001, Nature 409:207-211.
Srinivasula et al., 1998, Mol. Cell 1:949-957.
Terwilliger et al., 1999, Acta Crystallogr. D55:849-861.
Vaughn et al., 1999, J. Mol. Biol. 293:439-447.
Wang, 2004, J. Struct. Biol. 148:259-267.
Yoshida et al., 1998, Cell 94:739-750.
Yuan et al., 2000, Nature 407:802-809.
Yuan et al., 1992, Development 116:309-320.
Zhang et al., 2000, Mol. Cell 6:1473-1484.
Zhou et al., 1999, Mol. Cell 4:745-755.
Zhou et al., 1999, Proc. Natl. Acad. Sci. USA 96(20):11265-11270.
Zou et al., 1999, J. Boil. Chem. 274:11549-11556.
Zou et al., 1997, Cell 90:405-413.

* cited by examiner

*Primary Examiner*—Karen Cochrane Carlson
(74) *Attorney, Agent, or Firm*—Duane Morris LLP

(57) ABSTRACT

The structure of a soluble, functional fragment of human Apaf-1 protein having ADP bound thereto is disclosed. The invention includes such soluble, functional fragments of human Apaf-1 and other metazoan Apaf-1 homologs. Also included in the invention are methods of making such fragments and methods of using them, for example in screening methods to identify adenine nucleotide analogs and other compounds useful for alleviating or preventing disease conditions associated with inappropriate regulation of apoptosis.

15 Claims, 20 Drawing Sheets

(10 of 20 Drawing Sheet(s) Filed in Color)

```
  1 MDAKARNCLL QHREALEKDI KTSYIMDHMI SDGFLTISEE EKVRNEPTQQ QRAAMLIKMI
 61 LKKDNDSYVS FYNALLHEGY KDLAALLHDG IPVVSSSSGK DSVSGITSYV RTVLCEGGVP
121 QRPVVFVTRK KLVNAIQQKL SKLKGEPGWV TIHGMAGCGK SVLAAEAVRD HSLLEGCFPG
181 GVHWVSVGKQ DKSGLLMKLQ NLCTRLDQDE SFSQRLPLNI EEAKDRLRIL MLRKHPRSLL
241 ILDDVWDSWV LKAFDSQCQI LLTTRDKSVT DSVMGPKYVV PVESSLGKEK GLEILSLFVN
301 MKKADLPEQA HSIIKECKGS PLVVSLIGAL LRDFPNRWEY YLKQLQNKQF KRIRKSSSYD
361 YEALDEAMSI SVEMLREDIK DYYTDLSILQ KDVKVPTKVL CILWDMETEE VEDILQEFVN
421 KSLLFCDRNG KSFRYYLHDL QVDFLTEKNC SQLQDLHKKI ITQFQRYHQP HTLSPDQEDC
481 MYWYNFLAYH MASAKMHKEL CALMFSLDWI KAKTELVGPA HLIHEFVEYR HILDEKDCAV
541 SENFQEFLSL NGHLLGRQPF PNIVQLGLCE PETSEVYQQA KLQAKQEVDN G
```

Fig. 1

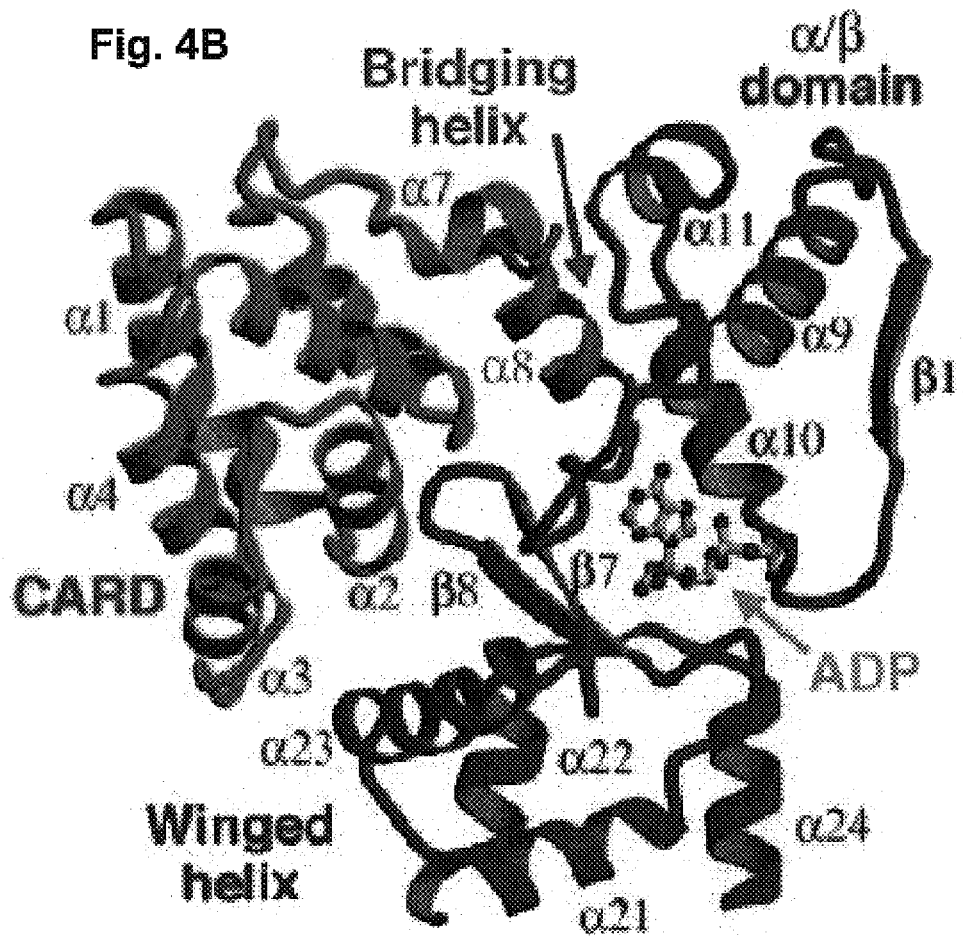

Fig. 6A

| Lane # | 1 | 2 | 3 | 4 | 5 | 6 | 7 |
|---|---|---|---|---|---|---|---|
| Caspase-9 | + | − | − | − | + | + | + |
| Apaf-1 | − | + | + | + | + | + | + |
| EDTA | − | − | + | + | + | + | − |
| Extra Mg²⁺ | − | − | − | + | + | − | − |

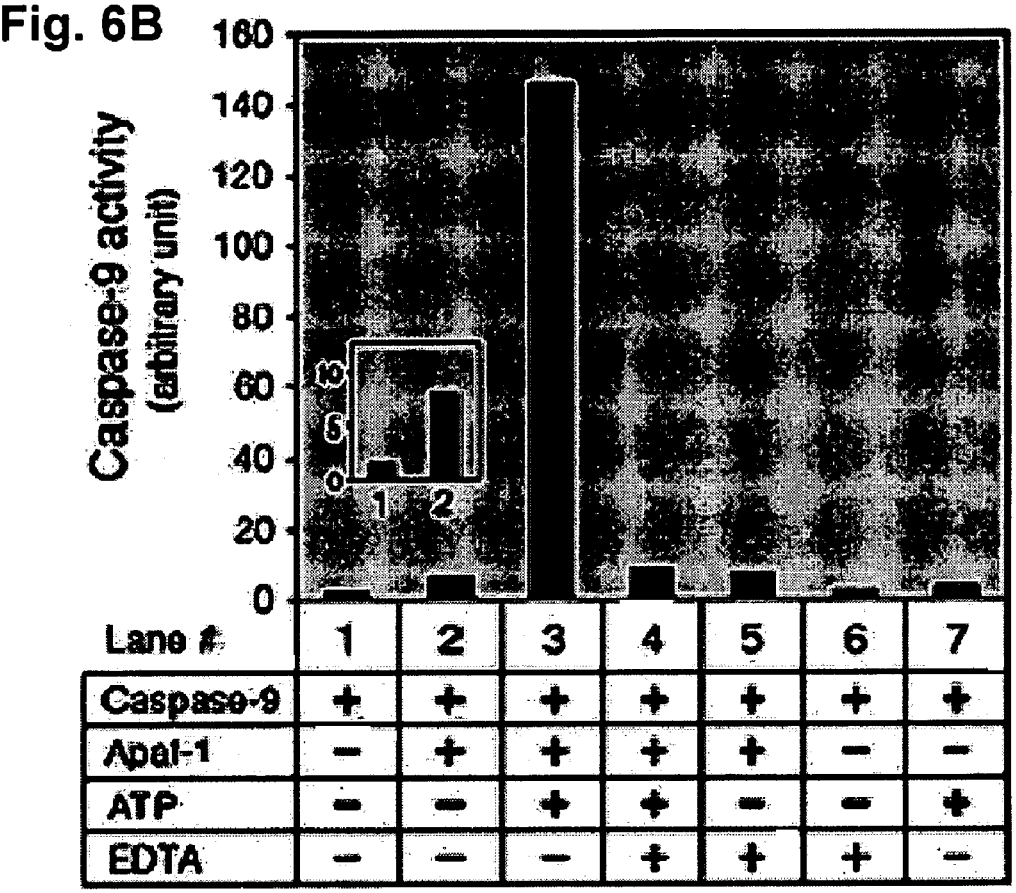

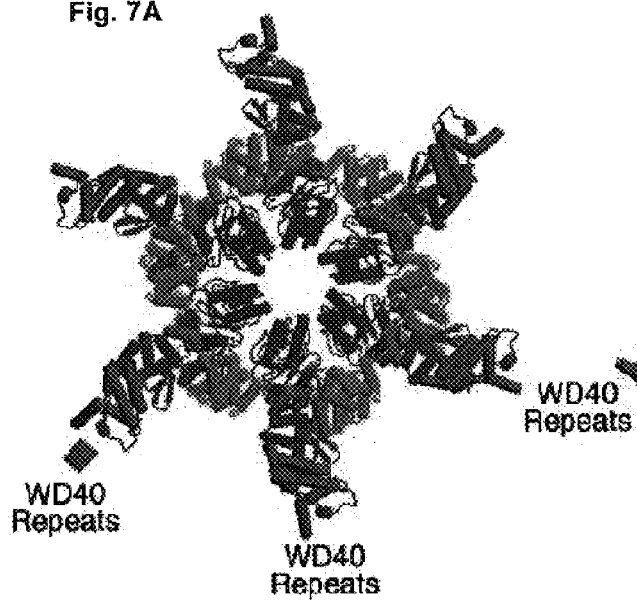
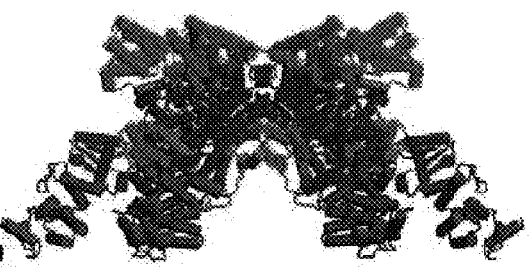
Fig. 7A
Fig. 7B

```
S     1  MDAKARNCLL  QHREALEKDI  KTSYIMDHMI  SDGFLTISEE  EKVRNEPTQQ  QRAAMLIKMI
LN    1  MDAKARNCLL  QHREALEKDI  KTSYIMDHMI  SDGFLTISEE  EKVRNEPTQQ  QRAAMLIKMI
LC    1  MDAKARNCLL  QHREALEKDI  KTSYIMDHMI  SDGFLTISEE  EKVRNEPTQQ  QRAAMLIKMI
XL    1  MDAKARNCLL  QHREALEKDI  KTSYIMDHMI  SDGFLTISEE  EKVRNEPTQQ  QRAAMLIKMI
SF    1  MDAKARNCLL  QHREALEKDI  KTSYIMDHMI  SDGFLTISEE  EKVRNEPTQQ  QRAAMLIKMI

S    61  LKKDNDSYVS  FYNALLHEGY  KDLAALLHDG  IPVVSSSSVR  TVLCEGGVPQ  RPVVFVTRKK
LN   61  LKKDNDSYVS  FYNALLHEGY  KDLAALLHDG  IPVVSSSSGK  DSVSGITSYV  RTVLCEGGVP
LC   61  LKKDNDSYVS  FYNALLHEGY  KDLAALLHDG  IPVVSSSSVR  TVLCEGGVPQ  RPVVFVTRKK
XL   61  LKKDNDSYVS  FYNALLHEGY  KDLAALLHDG  IPVVSSSSGK  DSVSGITSYV  RTVLCEGGVP
SF   61  LKKDNDSYVS  FYNALLHEGY  KDLAALLHDG  IPVVSSSSGK  DSVSGITSYV  RTVLCEGGVP

S   121  LVNAIQQKLS  KL--------  ---KGEPGWV  TIHGMAGCGK  SVLAAEAVRD  HSLLEGCFPG
LN  121  QRPVVFVTRK  KLVNAIQQKL  SKLKGEPGWV  TIHGMAGCGK  SVLAAEAVRD  HSLLEGCFPG
LC  121  LVNAIQQKLS  KL--------  ---KGEPGWV  TIHGMAGCGK  SVLAAEAVRD  HSLLEGCFPG
XL  121  QRPVVFVTRK  KLVNAIQQKL  SKLKGEPGWV  TIHGMAGCGK  SVLAAEAVRD  HSLLEGCFPG
SF  121  QRPVVFVTRK  KLVNAIQQKL  SKLKGEPGWV  TIHGMAGCGK  SVLAAEAVRD  HSLLEGCFPG
```

Fig. 8A

```
S   170 GVHWVSVGKQ DKSGLLMKLQ NLCTRLDQDE SFSQRLPLNI EEAKDRLRIL MLRKHPRSLL
LN  181 GVHWVSVGKQ DKSGLLMKLQ NLCTRLDQDE SFSQRLPLNI EEAKDRLRIL MLRKHPRSLL
LC  170 GVHWVSVGKQ DKSGLLMKLQ NLCTRLDQDE SFSQRLPLNI EEAKDRLRIL MLRKHPRSLL
XL  181 GVHWVSVGKQ DKSGLLMKLQ NLCTRLDQDE SFSQRLPLNI EEAKDRLRIL MLRKHPRSLL
SF  181 GVHWVSVGKQ DKSGLLMKLQ NLCTRLDQDE SFSQRLPLNI EEAKDRLRIL MLRKHPRSLL

S   230 ILDDVWDSWV LKAFDSQCQI LLTTRDKSVT DSVMGPKYVV PVESSLGKEK GLEILSLFVN
LN  241 ILDDVWDSWV LKAFDSQCQI LLTTRDKSVT DSVMGPKYVV PVESSLGKEK GLEILSLFVN
LC  230 ILDDVWDSWV LKAFDSQCQI LLTTRDKSVT DSVMGPKYVV PVESSLGKEK GLEILSLFVN
XL  241 ILDDVWDSWV LKAFDSQCQI LLTTRDKSVT DSVMGPKYVV PVESSLGKEK GLEILSLFVN
SF  241 ILDDVWDSWV LKAFDSQCQI LLTTRDKSVT DSVMGPKYVV PVESSLGKEK GLEILSLFVN

S   290 MKKADLPEQA HSIIKECKGS PLVVSLIGAL LRDFPNRWEY YLKQLQNKQF KRIRKSSSYD
LN  301 MKKADLPEQA HSIIKECKGS PLVVSLIGAL LRDFPNRWEY YLKQLQNKQF KRIRKSSSYD
LC  290 MKKADLPEQA HSIIKECKGS PLVVSLIGAL LRDFPNRWEY YLKQLQNKQF KRIRKSSSYD
XL  301 MKKADLPEQA HSIIKECKGS PLVVSLIGAL LRDFPNRWEY YLKQLQNKQF KRIRKSSSYD
SF  301 MKKADLPEQA HSIIKECKGS PLVVSLIGAL LRDFPNRWEY YLKQLQNKQF KRIRKSSSYD
```

Fig. 8B

```
S   350 YEALDEAMSI  SVEMLREDIK  DYYTDLSILQ  KDVKVPTKVL  CILWDMETEE  VEDILQEFVN
LN  361 YEALDEAMSI  SVEMLREDIK  DYYTDLSILQ  KDVKVPTKVL  CILWDMETEE  VEDILQEFVN
LC  350 YEALDEAMSI  SVEMLREDIK  DYYTDLSILQ  KDVKVPTKVL  CILWDMETEE  VEDILQEFVN
XL  361 YEALDEAMSI  SVEMLREDIK  DYYTDLSILQ  KDVKVPTKVL  CILWDMETEE  VEDILQEFVN
SF  361 YEALDEAMSI  SVEMLREDIK  DYYTDLSILQ  KDVKVPTKVL  CILWDMETEE  VEDILQEFVN

S   410 KSLLFCDRNG  KSFRYYLHDL  QVDFLTEKNC  SQLQDLHKKI  ITQFQRYHQP  HTLSPDQEDC
LN  421 KSLLFCDRNG  KSFRYYLHDL  QVDFLTEKNC  SQLQDLHKKI  ITQFQRYHQP  HTLSPDQEDC
LC  410 KSLLFCDRNG  KSFRYYLHDL  QVDFLTEKNC  SQLQDLHKKI  ITQFQRYHQP  HTLSPDQEDC
XL  421 KSLLFCDRNG  KSFRYYLHDL  QVDFLTEKNC  SQLQDLHKKI  ITQFQRYHQP  HTLSPDQEDC
SF  421 KSLLFCDRNG  KSFRYYLHDL  QVDFLTEKNC  SQLQDLHKKI  ITQFQRYHQP  HTLSPDQEDC

S   470 MYWYNFLAYH  MASAKMHKEL  CALMFSLDWI  KAKTELVGPA  HLIHEFVEYR  HILDEKDCAV
LN  481 MYWYNFLAYH  MASAKMHKEL  CALMFSLDWI  KAKTELVGPA  HLIHEFVEYR  HILDEKDCAV
LC  470 MYWYNFLAYH  MASAKMHKEL  CALMFSLDWI  KAKTELVGPA  HLIHEFVEYR  HILDEKDCAV
XL  481 MYWYNFLAYH  MASAKMHKEL  CALMFSLDWI  KAKTELVGPA  HLIHEFVEYR  HILDEKDCAV
SF  481 MYWYNFLAYH  MASAKMHKEL  CALMFSLDWI  KAKTELVGPA  HLIHEFVEYR  HILDEKDCAV
```

Fig. 8C

```
S   530  SENFQEFLSL  NGHLLGRQPF  PNIVQLGLCE  PETSEVYQQA  KLQAKQEVDN  GMLYLEWINK
LN  541  SENFQEFLSL  NGHLLGRQPF  PNIVQLGLCE  PETSEVYQQA  KLQAKQEVDN  GMLYLEWINK
LC  530  SENFQEFLSL  NGHLLGRQPF  PNIVQLGLCE  PETSEVYQQA  KLQAKQEVDN  GMLYLEWINK
XL  541  SENFQEFLSL  NGHLLGRQPF  PNIVQLGLCE  PETSEVYQQA  KLQAKQEVDN  GMLYLEWINK
SF  541  SENFQEFLSL  NGHLLGRQPF  PNIVQLGLCE  PETSEVYQQA  KLQAKQEVDN  G

S   590  KNITNLSRLV  VRPHTDAVYH  ACFSEDGQRI  ASCGADKTLQ  VFKAETGEKL  LEIKAHEDEV
LN  601  KNITNLSRLV  VRPHTDAVYH  ACFSEDGQRI  ASCGADKTLQ  VFKAETGEKL  LEIKAHEDEV
LC  590  KNITNLSRLV  VRPHTDAVYH  ACFSEDGQRI  ASCGADKTLQ  VFKAETGEKL  LEIKAHEDEV
XL  601  KNITNLSRLV  VRPHTDAVYH  ACFSEDGQRI  ASCGADKTLQ  VFKAETGEKL  LEIKAHEDEV

S   650  LCCAFSTDDR  FIATCSVDKK  VKIWNSMTGE  LVHTYDEHSE  QVNCCHFTNS  SHHLLLATGS
LN  661  LCCAFSTDDR  FIATCSVDKK  VKIWNSMTGE  LVHTYDEHSE  QVNCCHFANS  SHHLLLATGS
LC  650  LCCAFSTDDR  FIATCSVDKK  VKIWNSMTGE  LVHTYDEHSE  QVNCCHFTNS  SHHLLLATGS
XL  661  LCCAFSTDDR  FIATCSVDKK  VKIWNSMTGE  LVHTYDEHSE  QVNCCHFTNS  SHHLLLATGS

S   710  SDCFLKLWDL  NQKECRNTMF  GHTNSVNHCR  FSPDDKLLAS  CSADGTLKLW  DATSANERKS
LN  721  SDCFLKLWDL  NQKECRNTMF  GHTNSVNHCR  FSPDDKLLAS  CSADGTLKLW  DATSANERKS
LC  710  SDCFLKLWDL  NQKECRNTMF  GHTNSVNHCR  FSPDDKLLAS  CSADGTLKLW  DATSANERKS
XL  721  SDCFLKLWDL  NQKECRNTMF  GHTNSVNHCR  FSPDDKLLAS  CSADGTLKLW  DATSANERKS
```

Fig. 8D

| | | | | | | |
|---|---|---|---|---|---|---|
| S | 770 | INVKQFFLNL | EDPQEDMEVI | VKCCSWSADG | ARIMVAAKNK | IFL------- | ---------- |
| LN | 781 | INVKQFFLNL | EDPQEDMEVI | VKCCSWSADG | ARIMVAAKNK | IFL------- | ---------- |
| LC | 770 | INVKQFFLNL | EDPQEDMEVI | VKCCSWSADG | ARIMVAAKNK | IFLFDIHTSG | LLGEIHTGHH |
| XL | 781 | INVKQFFLNL | EDPQEDMEVI | VKCCSWSADG | ARIMVAAKNK | IFLFDIHTSG | LLGEIHTGHH |
| S | 813 | ---------- | ---------- | ----WNTD | SRSKVADCRG | HLSWVHGVMF | SPDGSSFLTS |
| LN | 824 | ---------- | ---------- | ----WNTD | SRSKVADCRG | HLSWVHGVMF | SPDGSSFLTS |
| LC | 830 | STIQYCDFSP | QNHLAVVALS | QYCVELWNTD | SRSKVADCRG | HLSWVHGVMF | SPDGSSFLTS |
| XL | 841 | STIQYCDFSP | QNHLAVVALS | QYCVELWNTD | SRSKVADCRG | HLSWVHGVMF | SPDGSSFLTS |
| S | 847 | SDDQTIRLWE | TKKVCKNSAV | MLKQEVDVVF | QENEVMVLAV | DHIRRLQLIN | GRTGQIDYLT |
| LN | 858 | SDDQTIRLWE | TKKVCKNSAV | MLKQEVDVVF | QENEVMVLAV | DHIRRLQLIN | GRTGQIDYLT |
| LC | 890 | SDDQTIRLWE | TKKVCKNSAV | MLKQEVDVVF | QENEVMVLAV | DHIRRLQLIN | GRTGQIDYLT |
| XL | 901 | SDDQTIRLWE | TKKVCKNSAV | MLKQEVDVVF | QENEVMVLAV | DHIRRLQLIN | GRTGQIDYLT |
| S | 907 | EAQVSCCCLS | PHLQYIAFGD | ENGAIEILEL | VNNRIFQSRF | QHKKTVWHIQ | FTADEKTLIS |
| LN | 918 | EAQVSCCCLS | PHLQYIAFGD | ENGAIEILEL | VNNRIFQSRF | QHKKTVWHIQ | FTADEKTLIS |
| LC | 950 | EAQVSCCCLS | PHLQYIAFGD | ENGAIEILEL | VNNRIFQSRF | QHKKTVWHIQ | FTADEKTLIS |
| XL | 961 | EAQVSCCCLS | PHLQYIAFGD | ENGAIEILEL | VNNRIFQSRF | QHKKTVWHIQ | FTADEKTLIS |

Fig. 8E

```
S     967 SSDDAEIQVW NWQLDKCIFL RGHQETVKDF RLLKNSRLLS WSFDGTVKVW NIITGNKEKD
LN    978 SSDDAEIQVW NWQLDKCIFL RGHQETVKDF RLLKNSRLLS WSFDGTVKVW NIITGNKEKD
LC   1010 SSDDAEIQVW NWQLDKCIFL RGHQETVKDF RLLKNSRLLS WSFDGTVKVW NIITGNKEKD
XL   1021 SSDDAEIQVW NWQLDKCIFL RGHQETVKDF RLLKNSRLLS WSFDGTVKVW NIITGNKEKD

S    1027 FVCHQGTVLS CDISHDATKF SSTSADKTAK IWSFDLLLPL HELRGHNGCV RCSAFSVDST
LN   1038 FVCHQGTVLS CDISHDATKF SSTSADKTAK IWSFDLLLPL HELRGHNGCV RCSAFSVDST
LC   1070 FVCHQGTVLS CDISHDATKF SSTSADKTAK IWSFDLLLPL HELRGHNGCV RCSAFSVDST
XL   1081 FVCHQGTVLS CDISHDATKF SSTSADKTAK IWSFDLLLPL HELRGHNGCV RCSAFSVDST

S    1087 LLATGDDNGE IRIWNVSNGE LLHLCAPLSE EGAATHGGWV TDLCFSPDGK MLISAGGYIK
LN   1098 LLATGDDNGE IRIWNVSNGE LLHLCAPLSE EGAATHGGWV TDLCFSPDGK MLISAGGYIK
LC   1130 LLATGDDNGE IRIWNVSNGE LLHLCAPLSE EGAATHGGWV TDLCFSPDGK MLISAGGYIK
XL   1141 LLATGDDNGE IRIWNVSNGE LLHLCAPLSE EGAATHGGWV TDLCFSPDGK MLISAGGYIK

S    1147 WWNVVTGESS QTFYTNGTNL KKIHVSPDFK TYVTVDNLGI LYILQTLE
LN   1158 WWNVVTGESS QTFYTNGTNL KKIHVSPDFK TYVTVDNLGI LYILQTLE
LC   1190 WWNVVTGESS QTFYTNGTNL KKIHVSPDFK TYVTVDNLGI LYILQTLE
XL   1201 WWNVVTGESS QTFYTNGTNL KKIHVSPDFK TYVTVDNLGI LYILQTLE
```

Fig. 8F

SOLUBLE, FUNCTIONAL APOPTOTIC PROTEASE-ACTIVATING FACTOR 1 FRAGMENTS

CROSS-REFERENCES TO RELATED APPLICATIONS

This application is entitled to priority pursuant to 35 U.S.C. §119(e) to U.S. provisional patent application 60/628,000, which was filed on 15 Nov. 2004.

STATEMENT REGARDING FEDERALLY SPONSORED RESEARCH OR DEVELOPMENT

This work was supported in part by grants from the National Institutes of Health (NIH Grants Nos. RO1 CA090269 and RO1 CA095218) and the U.S. Government may therefore have certain rights in this invention.

BACKGROUND OF THE INVENTION

The invention relates generally to the field of modulating the activity of the apoptotic protease-activating factor 1 (Apaf-1), which is an essential component of the apoptotic mechanism in mammalian cells.

Programmed cell death, or apoptosis, is essential to the development and homeostasis of metazoans (Danial et al., 2004, Cell 116:205-219; Horvitz, 2003, Chembiochem. 4:697-711). Abnormal inhibition of apoptosis is a hallmark of cancer and autoimmune diseases, and excessive activation of cell death is implicated in neuro-degenerative and other disorders (Hanahan et al., 2000, Cell 100:57-70; Yuan et al., 2000, Nature 407:802-809; Green et al., 2002, Cancer Cell 1: 19-30). Caspases, named after cysteine proteases that cleave after an aspartate residue in their substrates, are central components of the apoptotic response. The conserved mechanism of apoptosis across species involves a cascade of sequential activation of initiator and effector caspases (Riedl et al., 2004, Nature Rev. Mol. Cell. Biol. 5:897-907).

The caspase activation cascade downstream of mitochondria is controlled by Apaf-1, which is responsible for the activation of the initiator caspase-9 and subsequent activation of effector caspases-3 and -7 (Zou et al., 1997, Cell 90:405-413; Li et al., 1997, Cell 91:479-489). Apaf-1 has an essential role in the regulation of programmed cell death in mammalian development and in oncogene- and p53-dependent apoptosis (Cecconi et al., 1998, Cell 94:727-737; Yoshida et al., 1998, Cell 94:739-750; Soengas et al., 1999, Science 284:156-159; Fearnhead et al., 1998, Proc. Natl. Acad. Sci. 95:13664-1366). The importance of Apaf-1-mediated apoptosis is manifested by the observation that Apaf-1 is frequently inactivated in cancers such as malignant melanoma (Soengas et al., 2001, Nature 409:207-211).

In response to a wide range of intrinsic cell death stimuli, Apaf-1 interacts with cytosolic cytochrome c that is released from mitochondria and, in the presence of dATP or ATP, forms an oligomeric complex dubbed the apoptosome (Li et al., 1997, Cell 91:479-489; Zou et al., 1999, J. Biol. Chem. 274:11549-11556; Saleh et al., 1999, J. Biol. Chem. 274: 17941-17945; Hu et al., 1999, EMBO J. 18:3586-3595). The mechanistic role of ATP/dATP-binding to Apaf-1 is unknown, although it is essential to the formation of the apoptosome (Li et al., 1997, Cell 91:479-489; Zou et al., 1999, J. Biol. Chem. 274:11549-11556; Saleh et al., 1999, J. Biol. Chem. 274:17941-17945; Hu et al., 1999, EMBO J. 18:3586-3595; Jiang et al., 2000, J. Biol. Chem. 275:31199-31203). The apoptosome, in turn, recruits and activates pro-caspase-9 and forms a holoenzyme with the processed caspase-9 (Rodriguez et al., 1999, Genes Dev. 13:3179-3184). In *Drosophila*, the Apaf-1 orthologue Dark (also known as Dapaf-1 and Hac-1; Rodriguez et al., 1999, Nat. Cell Biol. 1:272-279; Kanuka et al., 1999, Mol. Cell 4:757-769; Zhou et al., 1999, Mol. Cell 4:745-755) is critically important for activation of the initiator caspase Dronc (a caspase-9 orthologue). In *C. elegans*, CED-4 exhibits significant sequence homology to Apaf-1 and is indispensable for the activation of CED-3 (Zou et al., 1997, Cell 90:405-413; Yuan et al., 1992, Development 116:309-320), the only apoptotic caspase in worms.

Apaf-1 is a 140-kilodalton, multi-domain protein, consisting of an N-terminal caspase recruitment domain (CARD), a central nucleotide-binding domain, and 12-13 repeats of the WD40 domain at the C-terminal half. The WD40 repeats are thought to be responsible for binding to cytochrome c and are believed to have a regulatory role in Apaf-1 function, because the removal of the WD40 repeats resulted in a constitutively active Apaf-1 protein that activated caspase-9 in a cytochrome c-independent manner (Hu et al., 1998, J. Biol. Chem. 273:33489-33494; Srinivasula et al., 1998, Mol. Cell 1:949-957). However, the underlying molecular mechanisms of how Apaf-1 interacts with ATP/dATP during formation of the apoptosome and activation of caspase-9 were not previously understood.

Apaf-1 is a representative member of the nucleotide-binding oligomerization (NOD) family of proteins that, in addition to Dark and CED-4, also include Ipaf, Nod1, Nod2, and a large family of disease-resistant proteins in plants (Inohara et al., 2001, Oncogene 20:6473-6481; Poyet et al., 2001, J. Biol. Chem. 276:28309-28313; Inohara et al., 1999, J. Biol. Chem. 274:14560-14567; Ogura et al., 2001, J. Biol. Chem. 276:4812-4818; Dangl et al., 2001, Nature 411:826-833). The hallmark of these proteins is the central NOD domain flanked by an N-terminal homotypic interaction motif and a C-terminal ligand-sensing domain. The shared domain structure suggests conserved mechanisms of action. However, the lack of structural information on any member of the NOD family proteins severely restricts our understanding on the mechanisms of the NOD family of proteins.

Efforts to study Apaf-1 protein have been hampered by inability of others to generate significant quantities of the protein in a form sufficiently stable, soluble, and pure to allow such study. For instance, there is no published protocol that allows bacterial expression and purification of a soluble recombinant Apaf-1 fragment longer than 200 amino acids. In addition, there is no published protocol that allows the preparation of a soluble, stable, recombinant Apaf-1 fragment longer than 200 amino acids, except for the full-length Apaf-1 protein in baculovirus-infected insect cells.

As a consequence of the lack of availability of reasonable quantities of Apaf-1 protein for research studies, little work has been done to identify compounds which can modulate the activity of Apaf-1. Furthermore, there has been an absence of three-dimensional structure information for any fragment of Apaf-1 other than the soluble N-terminal CARD domain. Knowledge of the physical structure of Apaf-1 protein would significantly aid design and screening of compounds that can modulate the activity of Apaf-1.

The present invention overcomes prior limitations by providing a method of producing stable, soluble, pure, and active Apaf-1 protein. The invention includes a description of the three-dimensional structure of Apaf-1 and methods of screening compounds to assess their ability to modulate Apaf-1 activity.

BRIEF SUMMARY OF THE INVENTION

The invention relates to soluble, activatable fragments of metazoan apoptotic protease-activating factor 1 (Apaf-1) proteins. Although human Apaf-1 is exemplified herein, the invention relates to analogous fragments of any metazoan Apaf-1, such as that of any chordate or of any mammal. The fragments comprise substantially the entire alpha/beta fold domain and at least most of the helical domain I of the factor and lack at least a portion of the WD40 repeat domain of the factor. Unlike the full-length Apaf-1 protein, the fragments described herein are soluble. Functionality is also preserved by including in the fragment at least the adenine nucleotide-binding region of Apaf-1. Caspase-activating activity of Apaf-1 is preserved if the CARD domain is also inclued. For instance, a soluble fragment of human Apaf-1 can be made that includes at least residues 94-349 of the human Apaf-1 sequence disclosed herein (i.e., residues 94-349 of SEQ ID NO: 1). Other examples of soluble Apaf-1 fragments include those which include at least residues 1-349, at least residues 94-589, or at least residues 1-591 of that sequence. Most or all of the WD40 repeat domain should be excluded from the fragments so that solubility of the fragment is not degraded.

The invention includes Apaf-1 fragments having conservative amino acid substitutions relative to the Apaf-1 sequences disclosed herein. The substitutions are those which do not significantly reduce the activity or solubility of the fragment, relative to the native sequence. Several suitable substitutions are disclosed herein, and others can be readily made by a skilled artisan.

The invention also relates to methods of making soluble recombinant activatable fragments of metazoan Apaf-1 proteins. In these methods, a host organism is transformed with an expression vector that is operable in the host organism. The vector includes a coding segment that is operably linked with the promoter/regulatory sequences of the vector. The coding segment encodes a protein fragment as described herein. In one embodiment, the coding segment also encodes a metal binding sequence linked to the fragment. Enhanced expression of the fragment can be obtained by culturing the host organism at a temperature lower than 37 degrees Celsius, such as a temperature in the range from 12-32 degrees Celsius. When the fragment is recombinantly expressed in the host organism, it can be isolated therefrom. Such isolation preferably is performed in the presence of a metal chelating agent.

The invention includes a variety of methods for assessing the ability of a compound to modulate activity of a metazoan Apaf-1. These methods can be performed by assessing the ability of the compound to affect an Apaf-1 protein fragment or an activity exhibited by such a fragment. For example, the ability of the compound to modulate the conformation of the fragment, hydrolysis of ATP catalyzed by the fragment, or activation of an apoptotic caspase (e.g., caspase-9) catalyzed by the fragment. In each instance, observing the phenomenon in the presence and absence of the phenomenon indicates the effect of the compound on the fragment and, by extension, on native Apaf-1.

BRIEF SUMMARY OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 1 is the amino acid sequence (SEQ ID NO: 1) of the 591-residue fragment of Apaf-1 expressed in *E. coli* strain BL21(DE3) and crystallized as described herein.

FIG. 2 comprises FIGS. 2A, 2B, and 2C. FIG. 2 was prepared using the MOLSCRIPT and GRASP software packages.

FIG. 4 comprises FIGS. 4A, 4B, and 4C. FIG. 4B is a ribbon plot showing packing between the CARD domain (shown in green in this figure) and the alpha/beta fold (shown in blue in this figure) and winged-helix (shown in pink in this figure) domains of the soluble Apaf-1 fragment. The bridging helix (shown in orange in this figure), which forms a single folding unit with the alpha/beta fold, closely stacks against helix alpha5 of the CARD domain. FIGS. 4A, 4B, and 4C were prepared using MOLSCRIPT and GRASP.

FIG. 6, comprising FIGS. 6A, 6B, and 6C, are a series of figures illustrating the ATPase and caspase-9-activating activities of Apaf-1.

FIG. 7, comprising FIGS. 7A and 7B, depicts a proposed model of the apoptosome, containing six copies of Apaf-1. The image in FIG. 7B is a view of the image in FIG. 7A, rotated 90 degrees along an axis in the plane of FIG. 7A. This predicted model of apoptosome is consistent with the observed three-dimensional contour of the apoptosome. The images in this figure were prepared using MOLSCRIPT and GRASP.

FIG. 8, comprising FIGS. 8A-8F, is a comparison of amino acid sequences of four Apaf-1 splice forms and a shorter soluble form described herein. The sequence designated "S" (SEQ ID NO: 2) is the shortest of the naturally-occurring splice forms disclosed herein. The sequence designated "LN" (SEQ ID NO: 3) differs from form S in that it has an 11-residue insertion following the CARD domain of form S. The sequence designated "LC" (SEQ ID NO: 4) differs from form S in that it has a 43-residue insertion in the WD40 repeats region of form S. The sequence designated "XL" (SEQ ID NO: 5) differs from form S in that it has both the 11-residue insertion following the CARD domain and the 43-residue insertion in the WD40 repeats region of form S. The sequence designated "SF (SEQ ID NO: 1) is the sequence of the soluble Apaf-1 fragment made recombinantly as described herein in Example 2.

DETAILED DESCRIPTION OF THE INVENTION

Figure 2A:
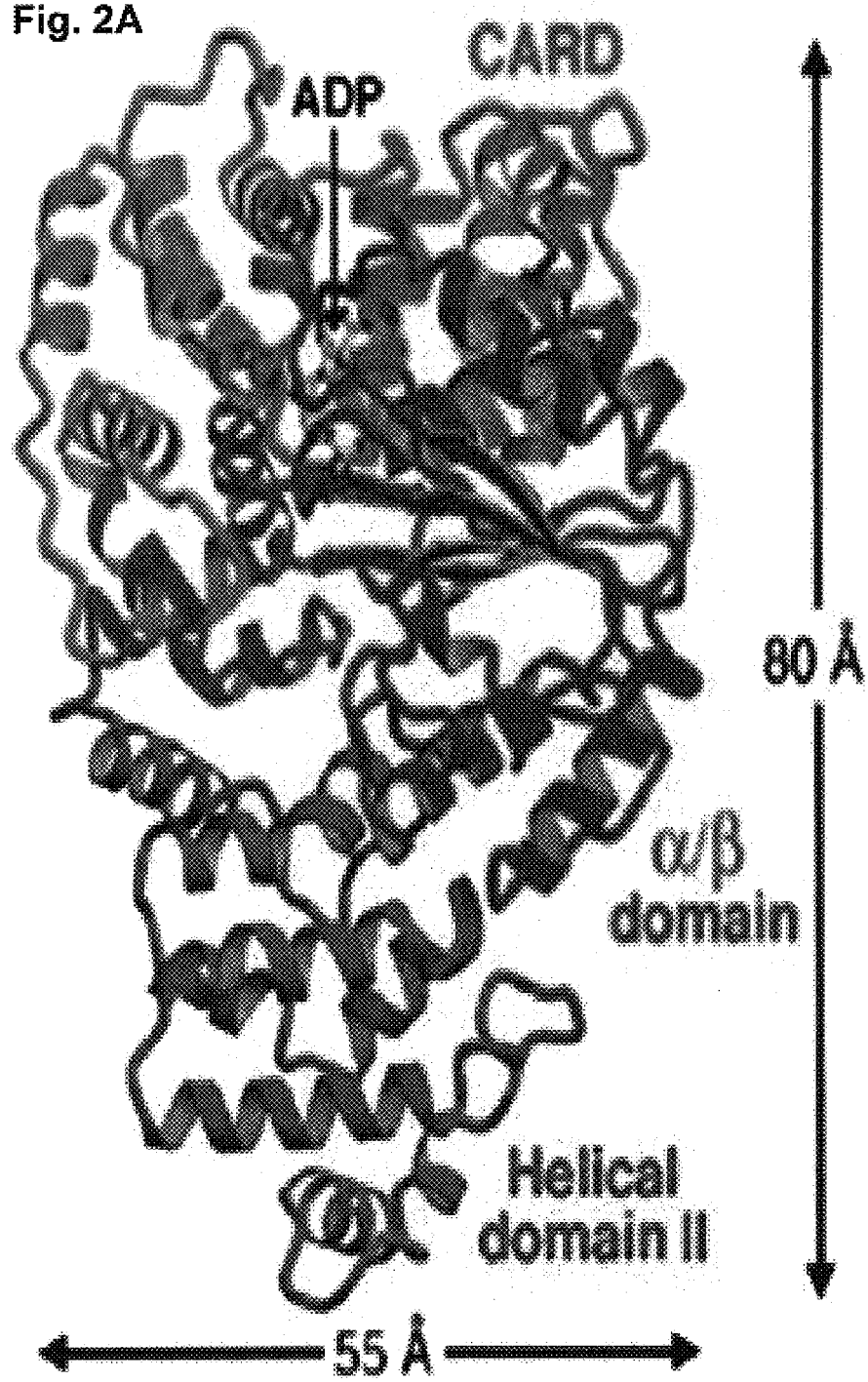
FIGS. 2A and 2B are a pair of ribbon diagrams of the overall structure of Apaf-1 bound to ADP. Apaf-1 comprises five distinct domains, the caspase recruitment domain (CARD, colored green in the Figure), an alpha/beta fold (colored blue in the Figure), a short alpha helical domain (helical domain I, colored cyan in the Figure), a winged-helix domain (colored magenta in the Figure), and an extended alpha helical domain (helical domain II, colored red in the Figure). These five domains pack closely against each other to generate a relatively compact structure, approximately 80 Angstroms in length, 55 Angstroms in width, and 65 Angstrom in thickness. ADP (colored yellow in the Figure) binds to the hinge region between the alpha/beta fold and helical domain I but is also coordinated by two critical residues from the winged helix domain. The structure of Apaf-1 shown in FIG. 2B is rotated 90 degrees (relative to the structure in FIG. 2A) around a vertical axis in the plane of the Figure.

Abnormal inhibition of apoptosis is a hallmark of cancer and autoimmune diseases, whereas excessive activation of cell death is implicated in neuro-degenerative disorders such as Alzheimer's Disease. Apoptosis involves the enzymatic activity of a family of specialized proteases known as "caspases." Caspases are synthesized as inactive zymogens and must be proteolytically processed to become fully active.

Human apoptotic protease activating factor 1 (Apaf-1) is a known activator of caspase proteins and an important component of the apoptotic response in human cells. Analogs of human Apaf-1 appear to exist in most, if not all, metazoans. Apaf-1 is responsible for activation of the initiator caspase-9 and subsequent activation of effector caspases-3 and -7. Apaf-1 plays an essential role in the regulation of programmed cell death in mammalian development and in oncogene- and p53-dependent apoptosis. The critical importance of Apaf-1-mediated apoptosis is manifested by the observation that Apaf-1 is frequently inactivated in cancers such as malignant melanoma.

For these reasons, there has been intense interest in studying Apaf-1, its activity, and its role in human disease. However, because the protein could not previously be isolated from human cells in a practical way and because no practical method existed previously for bacterial production of soluble recombinant forms of the protein, knowledge of Apaf-1 and its significance has been severely limited.

The invention relates to discovery of a soluble recombinant form of Apaf-1 protein and its analogs that retains its nucleotide-binding and caspase-activating activities. The invention also relates to methods of producing these recombinant proteins and methods of using them, for example to identify compounds capable of modulating their activity.

The invention also relates to the crystal structure of Apaf-1 bound to ADP, which provides the first glimpse of this important protein at atomic resolution (2.2 Angstroms). The structure reveals, unexpectedly, that the nucleotide-binding pocket of Apaf-1 is much larger than the bound ADP and that the pocket is lined by amino acid residues that are positioned to make specific interactions. These structural observations indicate that particular nucleotide analogs can be synthesized to occupy the nucleotide-binding pocket of Apaf-1. Biochemical evidence presented herein shows that binding to this pocket directly impacts the ability of Apaf-1 to activate caspase-9. Hence these novel structural features can be used to design nucleotide analogs that either enhance or inhibit activation of caspase-9 by Apaf-1. This information has profound implications for the treatment of cancer and other apoptosis-related diseases.

Definitions

As used herein, each of the following terms has the meaning associated with it in this section.

An Apaf-1 fragment is "soluble" if at least at least 10% (by weight) of the fragment remains in the supernatant following lysis of cells used to produce the fragment and centrifugation of the lysate at 20,000×g for 40 minutes and if the fragment in the supernatant does not aggregate, as assessed by gel filtration chromatograpy, for example. Preferably, solubility of the fragment is assessed in a lysate of a bacterial culture used to produce the fragment at a concentration of at least 1 milligram per liter of bacterial culture.

An Apaf-1 fragment is "funtional" if the fragment exhibits both i) the ability to bind ADP and ATP and ii) the ability to activate caspase-9 following binding of ATP to the fragment.

Soluble Recombinant Protein Fragments

Figure 3A:
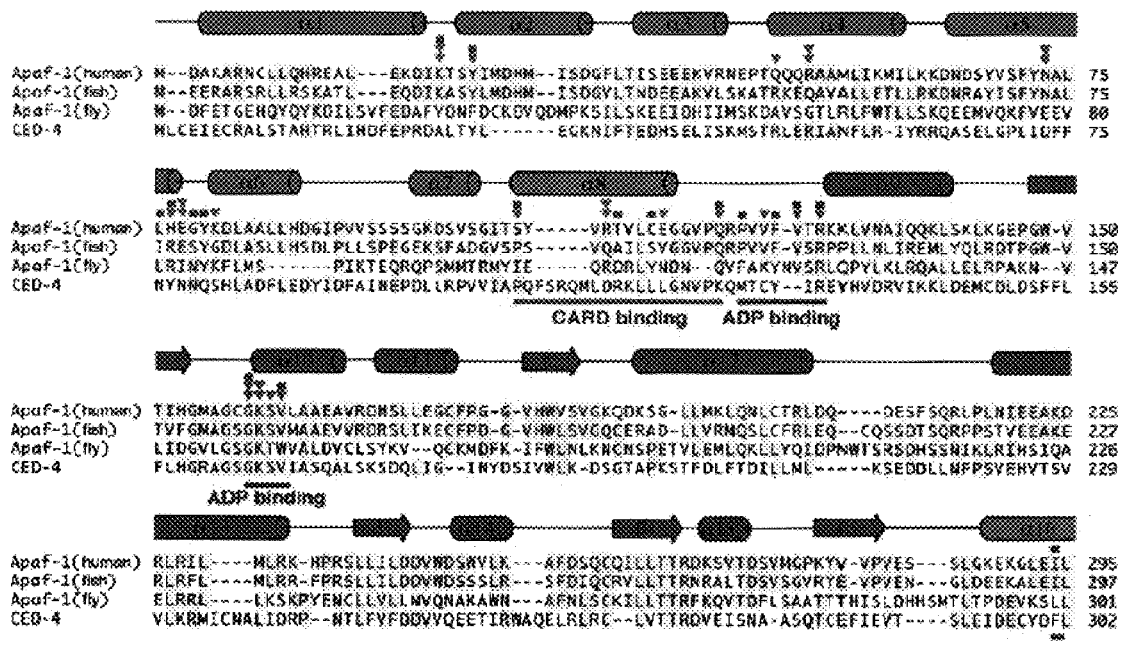
FIGS. 3A and 3B are an alignment of the sequences of the soluble human Apaf-1 protein fragment described in this example (SEQ ID NO: 1; "Apaf-1 (human)") and the corresponding sequences of its homologues in fish (residues 1-593; SEQ ID NO: 6; "Apaf-1(fish)"), fly (residues 1-588; SEQ ID NO: 7; "Apaf-1(fly)") and worm (residues 1-549; SEQ ID NO: 8; "CED-4"). The alignment was generated using the CLUSTALW software package. The secondary structural elements are color-coded based on their domain affiliation (i.e., using the same color scheme as in FIG. 2) and indicated above the alignment. Amino acid residues that are involved in inter-domain hydrogen bond and van der Waals contact with CARD are shown by blue arrows and magenta squares, respectively. Amino acid residues that bind to ADP through hydrogen bond and van der Waals contact are identified by magenta arrows and blue squares, respectively.
Figure 3B:
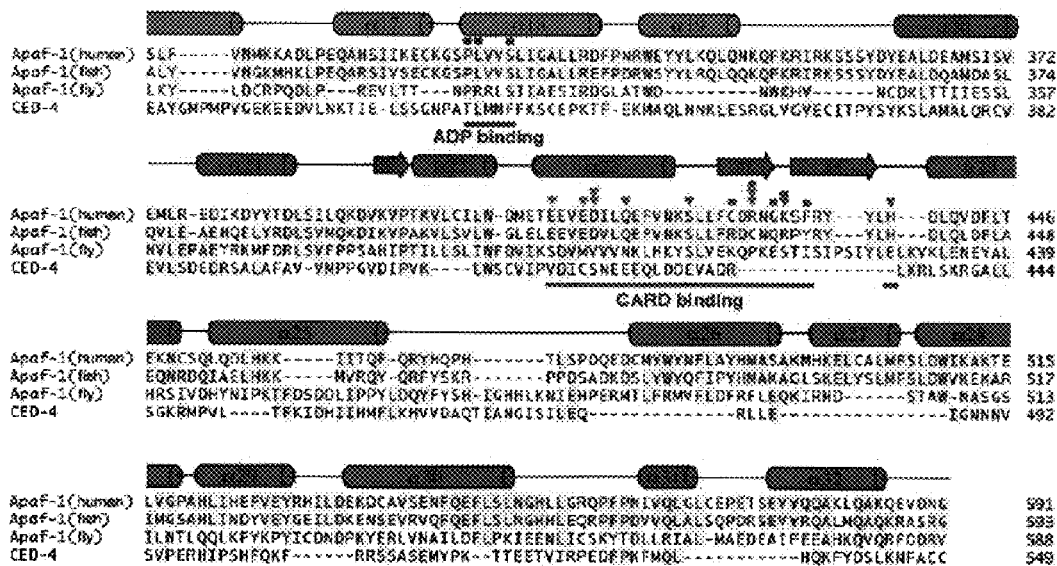

Previously, others have been unable to isolate recombinant Apaf-1 protein in a soluble, functional form from bacteria. It has been discovered that a recombinant fraction of Apaf-1 protein can be overexpressed in bacteria and isolated in a soluble, functional form. This soluble fragment retains the nucleotide-binding and caspase-activating activities of native Apaf-1 protein. Furthermore, given the amino acid sequence homology and similarity among metazoan Apaf-1 homologs (e.g., the similarity of human, fish, and fly Apaf-1 and worm CED-4 proteins is shown in FIG. 3), soluble active factors can be made from substantially any metazoan Apaf-1 homolog by analogy to the fragments made from human Apaf-1.

Human Apaf-1 consists of several distinct protein domains. Beginning at the amino-terminus, these domains are a CARD domain, an alpha/beta fold domain, an alpha-helical domain designated helical domain I, a winged helix domain, a second alpha-helical domain designated helical domain II, and a carboxyl-terminal WD40 repeat domain. A bridging helix designated alpha8 is interposed between the CARD and alpha/beta fold domains. It has been determined that the adenine nucleotide-binding region of human Apaf-1 involves the alpha/beta fold domain and at least most of helical domain I (possibly excluding alpha helix 19, as shown in FIG. 3). Thus, these portions of human Apaf-1 represent the minimum portion that must be present in order for the protein fragment to exhibit its nucleotide-binding and nucleotide hydrolysis-dependent activation characteristics. The bridging helix is also included in the protein fragment, because it forms a single folding unit with the alpha/beta fold domain.

In one embodiment, the invention includes an isolated, soluble, activatable fragment of human Apaf-1 protein that includes at least residues 144-333 of SEQ ID NO: 1 (i.e., a portion of the alpha/beta fold domain that does not include alpha helix 9 and a portion of helical domain I that does not include alpha helix 19). Preferred fragments include fragments having the amino acid sequence of SEQ ID NO: 1, beginning with an amino terminus at any of residues 1, 94, and 108 and having a carboxyl terminus at any of residues 333, 349, 469, 554, 567, 570, 589, 591, 611, and 650.

Human Apaf-1 exhibits a splice variant that affects the sequence of residues 99-143 of SEQ ID NOs: 1, 3, and 5 and residues 99-132 of SEQ ID NOs: 2 and 4 (compare residues 99-143 of the sequence identified as "SF" with residues 99-132 of the sequence identified as "S" in FIG. 8). The human Apaf-1 fragments of the invention can have the sequence of either splice variant in the region corresponding to 99-143 of SEQ ID NO: 1. Another splice variant manifests itself as an insertion of 43 amino acid residues between residues 812 and 813 of SEQ ID NO: 2 (corresponding to an insertion between residues 823 and 824 of SEQ ID NO: 3, the insertion corresponding to residues 813-855 of SEQ ID NO: 4 and to residues 824-866 of SEQ ID NO: 5).

Residue 115 (i.e., a cysteine residue) in SEQ ID NO: 1 can be substituted with a serine residue. Residue 568 in SEQ ID NO: 1 (i.e., a cysteine residue corresponding to residue 557 in SEQ ID NOs: 2 and 4) can also be substituted with a serine residue. Substitution of residue 160 in SEQ ID NO: 1 (i.e., a lysine residue corresponding to residue 149 in SEQ ID NOs: 2 and 4) with an arginine residue lowers expression and solubility of the resulting fragment, but nonetheless results in a soluble fragment.

The CARD domain of Apaf-1 is necessary in order for a recombinant fragment of Apaf-1 to exhibit its caspase-activating activity. In order to obtain a soluble recombinant protein fragment, it is necessary that most or all of the carboxyl-terminal WD40 repeat domain be absent from the protein. Suitable recombinant protein fragments preferably include substantially the entire helical domain I, and can include the winged helix and helical domain II domains of the factor.

The Apaf-1 fragments of the invention lack most (preferably all) of the WD40 repeat domain of the corresponding native protein. For example, the WD40 repeat domain begins in the neighborhood of residues 600-620 of SEQ ID NOs: 1 and 3, and extends substantially through to the carboxyl-terminus of the protein, including 12-13 copies of WD40 domains (depending on the splice variant). The data presented herein demonstrate that soluble, functional fragments can be generated which completely lack any portion of the WD40 repeat domain (e.g., fragment 1-591 in Table 2). Fragments containing a portion of the WD40 repeat domain extending through at least residue 611 of SEQ ID NO: 3 have been generated and exhibit suitable solubility and function, and it is believed that inclusion of a portion of the WD40 repeat domain extending through at least residue 650 of SEQ ID NO: 3 will exhibit suitable solubility and function for the purposes described herein. A skilled artisan will understand that the maximum amount of the WD40 repeat domain that can be included in the protein fragments described herein is substantially limited by the desolubilizing effect of including increasingly large portions of this domain. Nonetheless, the skilled artisan will recognize that residue 650 of SEQ ID NO: 3 is not a definite boundary for the portion of the WD40 repeat domain that can be included, and that determination of such a boundary is a matter of routine experimentation, in view of the solubility required for any particular application.

Although only several Apaf-1 homologs from metazoans are explicitly exemplified in this application, it is apparent that soluble active protein fragments can be made from the same regions of substantially any metazoan Apaf-1 homolog that shares an analogous domain structure. By way of example, the sequences of regions of analogs of human Apaf-1 are shown in FIG. 8 for fish (*Danio rerio*), fly (*Drosophila melanogaster*), and worm (*Caenorhabditis elegans*).

The invention includes a soluble, activatable fragment of a metazoan Apaf-1, the fragment comprising substantially the entire alpha/beta fold domain and at least most of the helical domain I of the factor and lacking at least a portion of the WD40 repeat domain of the factor. The fragment preferably includes the bridging helix, and can include one or more of the CARD domain, the winged-helix domain, and the helical domain II of the factor. The fragment must lack at least most of, and preferably at least substantially all of, the WD40 repeat domain.

It is evident that the identity of many amino acid residues is not critical to the solubility, stability, or activity of human Apaf-1 protein. A skilled artisan is able, in view of the structural information presented herein, to select residues of human Apaf-1 or another metazoan Apaf-1 that can be substituted with a different amino acid residue. Similarly, in view of the information presented herein (e.g., in the figures and in Example 2), a skilled artisan is able to identify amino acid residues having relatively high significance for the structure, stability, or activity of Apaf-1 protein and avoid making amino acid substitutions at those positions. By way of example, substitution of a serine residue in place of one of the cysteine residues at positions 115 or 568 of SEQ ID NO: 1 does not significantly adversely affect the solubility or activity of the corresponding recombinant Apaf-1 protein fragment. Substitution of an arginine residue in place of the lysine residue at position 160 of SEQ ID NO: 1, by contrast, has a relatively greater detrimental effect on the solubility and expression of the corresponding fragment.

The soluble fragments of metazoan Apaf-1 described herein do not occur in nature. They can be produced by way of substantially any recombinant protein production method known in the art. That is, the fragments can be made by including a nucleic acid encoding the fragment in a suitable expression vector and transforming a host organism with the vector. The host organism and vector are selected to be compatible, such that the fragment is expressed from the vector in the host organism. A wide variety of host organisms and corresponding expression vectors are known in the art, and substantially any compatible host organism—expression vector pair can be used to generate the protein fragments described herein. A suitable expression vector encoding a fragment described herein will include a coding segment (encoding the fragment) operably linked with promoter/regulatory sequences sufficient to achieve expression of the fragment in the host organism. The expression vector can optionally include other transcription regulatory sequences (e.g., regions known to enhance or inhibit transcription in the host organism), indicator regions (e.g., an antibiotic-resistance gene to identify host organisms transformed with the vector), or other expression vectors known in the art. The transcript of the vector encoding the fragment can optionally include a region encoding a polypeptide linked to the fragment, such as a fusion protein, a polypeptide that directs the translated peptide to a particular cellular compartment or to the exterior of the cell (e.g., a signal peptide), or a polypeptide for facilitating recovery of the expressed fragment (e.g., a poly-histidine polypeptide suitable for binding a metal affinity chromatography medium). A wide variety of such polypeptides are known in the art, and substantially any of them may be linked with the Apaf-1 fragment described herein. Optionally, the peptide can be linked with the fragment by a specifically cleavable polypeptide region to facilitate removal of the peptide after expression of the peptide-linked fragment.

A recombinantly-expressed fragment can be recovered using substantially any protein purification method known in the art. Preferably, the fragment is linked with a ligand suitable for binding with an affinity chromatography medium, such as a hexahistidine sequence which is capable of complexation with a bound metal ion (e.g., see Sharma et al, 1991, Biotechnol. Appl. Biochem. 14:69-81). Use of an affinity tag of this sort simplifies recovery of the recombinant fragment and can improve the purity of the recovered fragment, relative to other protein purification methods. By way of example, a hexa-histidine tag can be added an end of the recombinant sequence to facilitate metal affinity chromotographic purification of the recombinant protein, and the tag can thereafter be cleaved using thrombin.

It has been discovered that reduction (or substantial elimination) of free metal ions in the media used for purification of the recombinant fragment can improve recovery of the functional fragment in a soluble form. Such reduction can be achieved by exclusion of metal ions from the media or, preferably, by including one or more chelating agents in the media. Many suitable chelating agents are known in the art, of which ethylenediamine tetraacetic acid (EDTA) is a suitable example. The media preferably include a chelating agent in significant excess (e.g., two-fold or more) of the known or anticipated concentration of metal ions in the media.

Another way to improve the yield of soluble, functional fragment obtained from a recombinant organism is to maintain a low incubation temperature. It has been discovered that improved recovery of functional recombinant fragment can be realized as the temperature at which the host organism is incubated during production of the recombinant fragment is reduced below 37 degrees Celsius, and preferably below 32 degrees Celsius. Greater recoveries were achieved at incubation temperatures of about 20 degrees Celsius and at 12 degrees Celsius than at 37 degrees Celsius. A skilled artisan is able to select a suitable incubation temperature based on the identity and temperature tolerance of the host organism selected for production of the fragment. In general, however, lower temperatures tend to increase recovery of the recombinant fragment in a soluble, functional form.

The invention includes a nucleic acid that encodes a soluble fragment of a metazoan Apaf-1 of the type described herein. The nucleic acid can have the nucleotide sequence of a naturally-occurring Apaf-1, separated from at least most of the WD40 domains-encoding portion of the naturally-occurring sequence. In view of the redundancy of the genetic code, a skilled artisan recognizes that the sequence of a nucleic acid encoding a particular fragment can vary from the naturally-occurring nucleotide sequence without altering the amino acid sequence of the encoded fragment. By way of example, a synonymous codon (i.e., one which encodes the same amino acid residue) can be used in place of a naturally-occurring codon when the nucleic acid is to be expressed in a host organism preferentially translates the synonymous codon relative to the naturally-occurring codon. Similarly, a skilled artisan will recognize that conservative amino acid residue substitutions can be encoded, corresponding to portions of the fragment for which the amino acid sequence is not identified herein as being important to functionality of the fragment. Thus, the invention include nucleic acids which encode a soluble, activatable fragment of a metazoan Apaf-1 encoded by a nucleic acid, wherein the nucleic acid is capable of hybridizing to a polynucleotide having the sequence of one of SEQ ID NOs: 1-8 under stringent hybridization conditions (e.g., during washing with a solution consisting of 15 millimolar sodium chloride, 1.5 millimolar sodium citrate, and 0.1% (w/v) sodium dodecylsulfate at 50 degrees Celsius).

Significant insolubility is a characteristic shared by many NOD proteins (Apaf-1 is a NOD protein). Many NOD proteins are believed to have a repeating carboxy-terminal portion that, in many instances, is not believed to significantly affect the activity of other protein domains nearer the amino terminus. By analogy to the methods described herein for making soluble, functional the Apaf-1 fragments, one can prepare recombinant fragments of other NOD proteins by removing most or all of the carboxy-terminal repeat domains from the NOD protein and recombinantly expressing the remainder of the protein in a bacterium. In this way, soluble, functional fragments of other NOD proteins can be prepared which are suitable for crystallization or other purposes described herein.

Screening Methods

The data reported herein indicate that activation of human Apaf-1 protein involves a conformation change that occurs upon binding and/or hydrolysis of an adenine nucleotide with Apaf-1. The binding site of the adenine nucleotide is identified in the data reported herein as being located in a portion of Apaf-1 that includes substantially the entire alpha/beta fold domain and at least most of the helical domain I of Apaf-1. Because this region of Apaf-1 appears to mediate most, if not all of the interaction of Apaf-1 with adenine nucleotides, observation of the effect of a nucleotide analog (or another compound) on this region is sufficient to predict the effect of the analog (or other compound) on activation of Apaf-1, and thereby the effect of the analog on caspase activation. Screening of compounds against a soluble fragment of Apaf-1 that includes at least this region is therefore a suitable method for assessing the effect of the compound on activation of Apaf-1 and its associated caspases. Such screening can be used to identify compound capable of therapeutic use in apoptosis-related disorders.

Because prior preparations of recombinant Apaf-1 from bacteria yielded little or no soluble, functional protein, they could not be practically used in such screening methods. The soluble, functional protein fragments described herein therefore represent an important advance in methods of identifying compounds suitable for treatment of disease conditions in which Apaf-1 has a role. Examples of such disorders include cancers such as malignant melanoma and neuro-degenerative disorders such as Alzheimer's disease.

The invention includes a method of assessing the ability of a compound to modulate activation of a metazoan Apaf-1 homolog. In this method, the compound is contacted with a soluble, activatable fragment of a metazoan Apaf-1 described herein and the conformation of the fragment is observed. Attainment of an open conformation by the fragment (i.e., a conformation wherein the fragment can form the apoptosome) is an indication that the compound activates the factor and attainment of a closed conformation by the fragment (analogous to the conformation of the ADP-bound Apaf-1 fragment described herein) is an indication that the compound inactivates the factor. The conformation of the fragment can be assessed in the presence of the compound alone. Alternatively, the conformation of the fragment can be assessed in the presence of an adenine nucleotide (e.g., ADP or ATP) having a known effect on the conformation, and the influence of the presence and absence of the compound on that known effect can be assessed.

Substantially any known method can be used to assess the conformation of the fragments described herein in the presence or absence of a compound. Examples of suitable techniques include fluorescence spectroscopy, light scattering analysis, size exclusion chromatography, and circular dichroism spectroscopy. X-ray crystallography and nuclear magnetic resonance spectroscopy can also be used to assess conformation. The ability of a compound to affect interaction of a human Apaf-1 fragment of the type described herein (or a soluble fragment of another metazoan Apaf-1) with an adenine nucleotide can be assessed directly (i.e., by assessing binding of a fluorescently- or radio-labeled nucleotide with the fragment, for example) or indirectly, by assessing Apaf-1-mediated hydrolysis of a hydrolyzable nucleotide in the presence and absence of the compound. Furthermore, the binding affinity of Apaf-1 toward an adenine nucleotide (e.g., ADP or ATP) can be assessed in the presence and absence of the compound. Lowered binding affinity for the adenine nucleotide is an indication that the compound binds with Apaf-1 in a way that inhibits adenine nucleotide binding. The kinetics of binding inhibition can be assessed in routine ways to yield further information about the mechanism (e.g., competetive or non-competetive) by which the compound inhibits adenine nucleotide binding, which can provide further information about the portion of the fragment with which the compound interacts.

If the fragment used in the screening assay comprises the CARD domain of the corresponding Apaf-1, then a caspase activation assay (of which many are known in the art) can be used to assess caspase-activating activity of the fragment in the presence and absence of the compound.

Therapeutic Compositions

The soluble, functional Apaf-1 fragments described herein can be administered to a cell or tissue of a patient in need of caspase activation. Such fragments can be suspended in a pharmaceutically acceptable carrier and administered to a body location at which Apaf-1 activity is needed. For tissues to which administration of a protein fragment described herein is not expected to be practical (e.g., where the fragment must be transported across the cytoplasmic membrane of a cell, a nucleic acid encoding such a fragment can be administered instead. A variety of suitable vectors (e.g., virus vectors and other vectors suitable for delivering a gene to the interior of a mammalian cell are known in the art, and substantially any of these vectors can be used to deliver an expression vector encoding a protein fragment described herein to a cell.

The three-dimensional Apaf-1 fragment structure disclosed herein can be used in computerized rational drug design (i.e., molecular modeling and molecule-molecule interaction modeling) methods to identify candidate compounds that bind with an active portion of Apaf-1. A variety of computerized drug design programs capable of modeling the interaction of a candidate compound with, for example, atomic coordinates described herein, are known in the art, and the operation of such programs is within the ken of the ordinary artisan in the field of rational drug design. Such methods can be used to design compounds that interact with the adenine nucleotide-binding portion of Apaf-1, the caspase-interacting (CARD) domain of Apaf-1, or portions of Apaf-1 which interact with one another (i.e., to disrupt Apaf-1 structure).

Candidate compounds can be designed based on the structure of a known ligand of Apaf-1. By way of example, adenine nucleotide analogs can be designed based on the structure of ADP or ATP for the purpose of designing an analog that will interact with the adenine nucleotide-binding portion of Apaf-1. Alternatively, the interaction with Apaf-1 of compounds in a library of known or modeled compounds can be assessed using the same rational drug design software. Iterative design methodologies can be employed, whereby a later generation of candidate compounds can be designed based on modeling data obtained with an earlier generation of candidate compounds (e.g., by modifying the structure of an earlier-generation compound for which the modeling software indicates strong Apaf-1-binding affinity).

A compound identified by rational drug design methods as likely exhibiting desirable interaction with Apaf-1 can thereafter be synthesized or purchased, and the compound's ability to interact with Apaf-1 in a desirable manner can be assessed experimentally. For example, compounds which are intended to modulate the activity of Apaf-1 can be assessed using any of the methods described herein.

Using the methods described herein, the crystal structure of a soluble Apaf-1 fragment having a candidate compound bound therewith can be assessed. This crystal structure information can be used to confirm that the compound binds with Apaf-1 in the manner suggested by the molecular modeling software used to design the compound. The crystal structure of a compound-bound soluble Apaf-1 fragment can also be used to design modifications of the compound structure that bind more or less strongly with Apaf-1, as described herein.

EXAMPLES

The invention is now described with reference to the following Examples. These Examples are provided for the purpose of illustration only, and the invention is not limited to these Examples, but rather encompasses all variations which are evident as a result of the teaching provided herein.

Example 1

Preparation of Soluble Recombinant Apaf-1 Protein

Prior to the experiments described herein, there was no published protocol that allows bacterial expression and purification of a soluble recombinant Apaf-1 fragment longer than 200 amino acids. There was also no published protocol that allows the preparation of any soluble, stable, recombinant Apaf-1 fragment longer than 200 amino acids except that for the full-length Apaf-1 protein produced in baculovirus-infected insect cells. The full-length protein produced in baculovirus exhibited low yield and significant conformational heterogeneity, and its usefulness for many purposes is limited.

In the experiments described herein, several factors were discovered that enhance the expression of soluble Apaf-1 protein fragments in bacteria.

Length of Apaf-1 Protein Fragment

It was discovered that an Apaf-1 fragment having its carboxyl-terminal boundary between amino acids 550 and 650 of the native protein exhibits better solution behavior than those with carboxyl-terminal boundaries prior to amino acids 550. The structure of Apaf-1 was used to determine the length of appropriate Apaf-1 fragments. For example, Apaf-1 (residues 1-589) exhibits greater solubility than Apaf-1 (1-349) or Apaf-1 (1-469) because Apaf-1 (1-349) and Apaf-1 (1-469) failed to maintain the structural integrity of Apaf-1. For example, the following recombinant Apaf-1 proteins, residues 1-611, 1-591, 1-589, 1-570, 1-567, and 1-554, all exhibit good solubility and solution behavior because they allow the fragment 1-591 to form an intact structural entity, as seen in the crystal structure. A summary of Apaf-1 fragments and their relative degrees of expression and solubility is included herein as Table 2.

The structure of Apaf-1, described herein for the first time, reveals the domain organization of Apaf-1. This information provides a useful guideline for the design of soluble recombinant constructs for Apaf-1. For example, the primary nucleotide-binding site is located between the alpha/beta fold (residues 108-284) and helical domain I (residues 285-365), indicating that any functional recombinant Apaf-1 fragment must contain, minimally, the entire alpha/beta fold and the bulk of the helical domain I in order to be soluble and functional. Indeed, non-functional recombinant Apaf-1 (residues 1-286) protein is largely insoluble while Apaf-1 (residues 1-349) is soluble to significant extent.

Skilled artisans will appreciate that conservative amino acid substitutions that do not significantly disrupt the domain structure of Apaf-1 or alter residues shown herein to be significant for inter-domain interactions or binding of adenine nucleotides can be made without significantly altering the functionality of the protein. By way of example, point mutations K160R, C115S, and C568S were made in SEQ ID NO: 1 without significant loss of activity or solubility.

Growth Conditions

Recovery of soluble, active recombinant Apaf-1 protein fragments can be increased by decreasing the temperature at which the recombinant organism is cultured below 32 degrees Celsius. Lowering the temperature progressively facilitates the production of soluble recombinant Apaf-1 protein. For example, at 27 degrees Celsius, some recombinant Apaf-1 protein can be expressed in soluble form, whereas at ambient temperatures (i.e., between 20 and 24 degrees Celsius), a greater portion of recombinant Apaf-1 protein is soluble. A growth temperature below 20 degrees Celsius (e.g., 4, 10, or 15 degrees Celsius) further improves expression and production of Apaf-1 protein.

Purification of Recombinant Apaf-1 in the Presence of EDTA

It was discovered that incubation with excess amounts (here, 2-5 millimolar) of EDTA allows recombinant Apaf-1 protein to be recovered as a more homogeneous population of molecules than if EDTA is not used. Without being bound by any particular theory of operation, the beneficial effect of EDTA is believed to be attributable to the metal-chelating ability of EDTA. Metal chelation can reduce the ability of recombinant Apaf-1 to change between various conformations having differing chromatographic and other behaviors. It is believed that substantially any chelator of metal ions will have a similar effect. Although the exact amount of chelator used is not critical, the amount should be sufficient to chelate substantially all metals present in the medium from which Apaf-1 is to be purified.

Example 2

Three-Dimensional Structure and Mechanism of Apaf-1

In this example, the 2.2-Angstrom three-dimensional structure of a functional fragment of Apaf-1 (residues 1-591) bound to adenosine diphosphate (ADP) is reported. This structure reveals, surprisingly, a closed conformation of Apaf-1. This structure provides a framework for understanding Apaf-1 function, apoptosome assembly, and caspase-9 activation. The information can also be used to decipher the general mechanisms of the NOD family of proteins.

The materials and methods used in this example are now described.

Protein Preparation

All constructs for protein expression were generated using a standard PCR-based cloning strategy, and the identity of individual clones was verified by double-stranded plasmid sequencing. A soluble Apaf-1 fragment (residues 1-591, sequence (SEQ ID NO: 1) shown in FIG. 1) was over-expressed in *Escherichia coli* strain BL21(DE3) using plasmid vector pET29 having the nucleotide sequence described by Jiang et al. (2000, J. Biol. Chem. 275:31199-31203) operatively ligated therein. The coding sequence included an additional sequence encoding eight amino acid residues at its carboxy-terminal end (i.e., linked to residue 591 in the translated protein). These residues (Leu-Glu-His$_6$) included a nickel-binding hexa-histidine sequence used for metal affinity chromatographic purification of the expressed protein. Soluble Apaf-1 was purified from the cell lysate using a Ni-NTA (nitrilotriacetic acid-ligated nickel; Qiagen) chromatography column. Dithiothreitol (DTT) and ethylenediamine tetraacetic acid (EDTA) were added to the eluted fraction in final concentrations of 5 millimolar each. After incubation for 30 minutes on ice, the protein solution was applied to an anion-exchange column (Source-15Q, Pharmacia) for further purification.

Recombinant full-length caspase-9 was also over-expressed in *E. coli* strain BL21(DE3) using pET29 having the sequence described in Srinivasula et al., (1998, Cell 1:949-957) operatively ligated therein. Recombinantly-expressed caspase-9 was purified in a manner analogous to that used for the soluble Apaf-1 fragment, with addition of a gel-filtration chromatography step (using SUPERDEX™-200 chromatography medium, Pharmacia).

Crystallization

Purified soluble Apaf-1 fragment obtained from anion-exchange chromatography was used directly for crystallization. The fragment was initially present at a concentration of about 3 milligrams per milliliter in 20 millimolar HEPES buffer, pH 7.8, containing 2 millimolar DTT. Crystals were produced using the sitting-drop vapor-diffusion method. Protein samples having a volume of 2 microliters were mixed with an equal volume of a reservoir solution containing 100 millimolar HEPES (pH 7.1), 250 millimolar ammonium acetate, and 19% (w/v) polyethylene glycol (PEG-3350), and with 1 microliter of 100 millimolar DTT. Crystals appeared after one- to three-weeks of storage at 4 degrees Celsius, with a typical crystal size of 0.1 millimeter×0.1 millimeter×0.1 millimeter.

Derivative crystals were obtained by soaking crystals overnight in mother liquor containing 1 millimolar mercury thimerosal followed by back-soaking for 5 minutes. Native and derivative crystals were then equilibrated in a cryo-protectant buffer containing well buffer plus 5% glycerol and were flash-frozen in liquid nitrogen. Derivative crystals belong to the space group P21, with unit cell dimensions of a=47.83 Angstrom, b=76.01 Angstrom, c=81.15 Angstrom, beta=91.33 degrees, and contained one protein molecule per asymmetric unit. Native crystals belong to the space group P1, with unit cell dimensions of a=75.96 Angstrom, b=92.88 Angstrom, c=94.99 Angstrom, alpha=62.96 degrees, beta=89.99 degrees, and gamma=90.05 degrees, and contained four molecules of Apaf-1 in one asymmetric unit (the unit cell).

Data Collection and Structure Determination

Anomalous diffraction data were collected at the National Synchrotron Light Source (NSLS) beamline X25 using three wavelengths corresponding to inflection point, high energy remote, and peak of a Hg-MAD experiment. In addition, a 2.2-Angstrom native data set was collected at the Cornell High Energy Synchrotron Source (CHESS) beamline A1. The data sets were collected at 100 K using Quantum 210 CCD detectors. Data were integrated, reduced, and scaled using HKL2000 (Otwinowski et al., 1997, Methods Enzymol. 276:307-326). The initial structure was determined using 3.1-Angstrom Hg-MAD data using SOLVE/RESOLVE (Terwilliger et al., 1999, Acta Crystallogr. D55:849-

861). Model building and TLS-refinement were performed using the 2.2-Angstrom native dataset using O (Jones et al., 1991, Acta Crystallogr. A47:110-119) and REFMAC5 (Collaborative Computational Project, 1994, The CCP4 suite: programs for protein crystallography, Acta Crystallogr. D50: 760-763). Tight and medium NCS restraints were imposed for main chain and side chain atoms, respectively. Data collection and refinement statistics are summarized in Table 1. The final atomic model includes four monomers (chains A, B, C, and D; corresponding to Apaf-1 residues 1-586), four ADP molecules, and 782 water molecules in the asymmetric unit. No electron density was observed for residues 587-591, or for residues 95-103 in chains A and B.

ATPase Assay

ATPase activity was determined using a thin layer chromatography (TLC) assay designed to quantitatively measure the conversion of (alpha-$^{32}$P)ATP to ADP. Reactions were initiated by mixing the soluble Apaf-1 fragment at a final concentration of 2 micromolar with a solution containing 20 millimolar HEPES, pH 7.5, 10 millimolar DTT, 10 micromolar magnesium chloride, 0.1 micromolar (alpha-$^{32}$P)ATP, and 8 micromolar ATP. The reaction was incubated at room temperature for the indicated duration and then quenched by addition of an equal volume of developing solvent (1 molar formic acid, 0.5 molar LiCl). Samples were evaluated based on the differential mobility of ATP versus ADP on TLC using polyethyleneimine-cellulose F plates.

Caspase-9 Activation Assay

A fluorogenic assay was developed to monitor caspase-9 activation by the soluble Apaf-1 fragment. ATP or another nucleotide or nucleotide analog was mixed with buffer (20 millimolar HEPES, pH 7.5, 100 millimolar KCl, 5 millimolar DTT) to a final concentration of 1 millimolar in the presence or absence of 1 millimolar EDTA. Then, caspase-9 and Apaf-1 were added to a final volume of 200 microliter and final concentrations of 0.2 micromolar and 2 micromolar, respectively. After incubation for 5 minutes at room temperature, the caspase-9 substrate LEHD-AMC (a tetrapeptide coupled to 7-amino 4-methoxycoumarin) was added to the reaction at a final concentration of 200 micromolar. The conversion of the fluorogenic substrate was then measured using a Hitachi F2500 fluorescence spectrophotometer with an excitation wavelength of 380 nanometers and a fluorescence detection wavelength of 440 nanometers.

The results obtained from the experiments in this example are now described.

Crystallization and Structure Determination

Full-length (ca. 140-kilodalton) Apaf-1 protein exhibited considerable conformational flexibility that impeded crystallization efforts. Because the removal of carboxyl-terminal WD40 repeats does not affect the ability of Apaf-1 to bind ATP/dATP, to form the apoptosome, or to activate caspase-9 (Hu et al., 1999, EMBO J. 18:3586-3595; Hu et al., 1998, J. Biol. Chem. 273:33489-33494; Srinivasula et al., 1998, Mol. Cell 1:949-957), functional fragments of Apaf-1 devoid of the WD40 repeats were selected for study.

We assessed the micro-conformational heterogeneity of the recombinant protein. We found that, when expressed in bacteria or in insect cells, Apaf-1 exists in more than one conformation, as judged by its solution behavior on ion-exchange chromatography media and in caspase-9 activation assays. It was determined that the conformational heterogeneity is largely contributed by the status of nucleotide binding and the intrinsic ATPase activity of Apaf-1. It was discovered that incubation of Apaf-1 with EDTA during recombinantly-produced protein purification yielded recombinant Apaf-1 protein in a single conformation. The homogeneous Apaf-1 protein (residues 1-591) was crystallized in the space group P1, with four molecules in each asymmetric unit.

The structure was determined by multi-wavelength anomalous dispersion (MAD) using anomalous signals from mercury (properties listed Table 1). The final atomic model of Apaf-1, which includes 586 amino acid residues, was refined at 2.2-Angstrom resolution. The atomic coordinates determined from the modeling are deposited with the Protein Data Bank and assigned the accession number 1Z6T.

The four molecules of Apaf-1 in each asymmetric unit exhibit identical structural features important for this discussion. For simplicity, the remaining discussion describes just one of the four molecules.

Overall Structure of Apaf-1

Figure 2B:
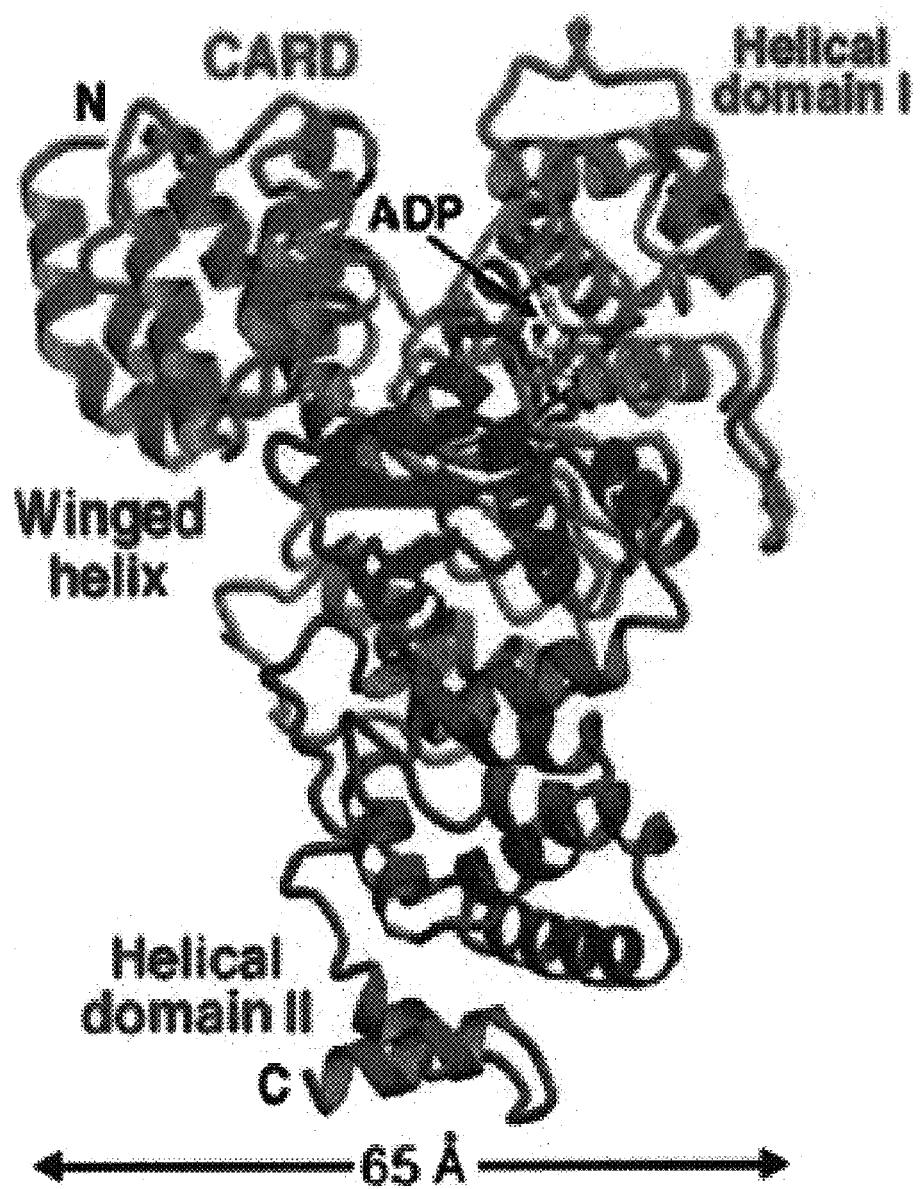
Figure 2C:
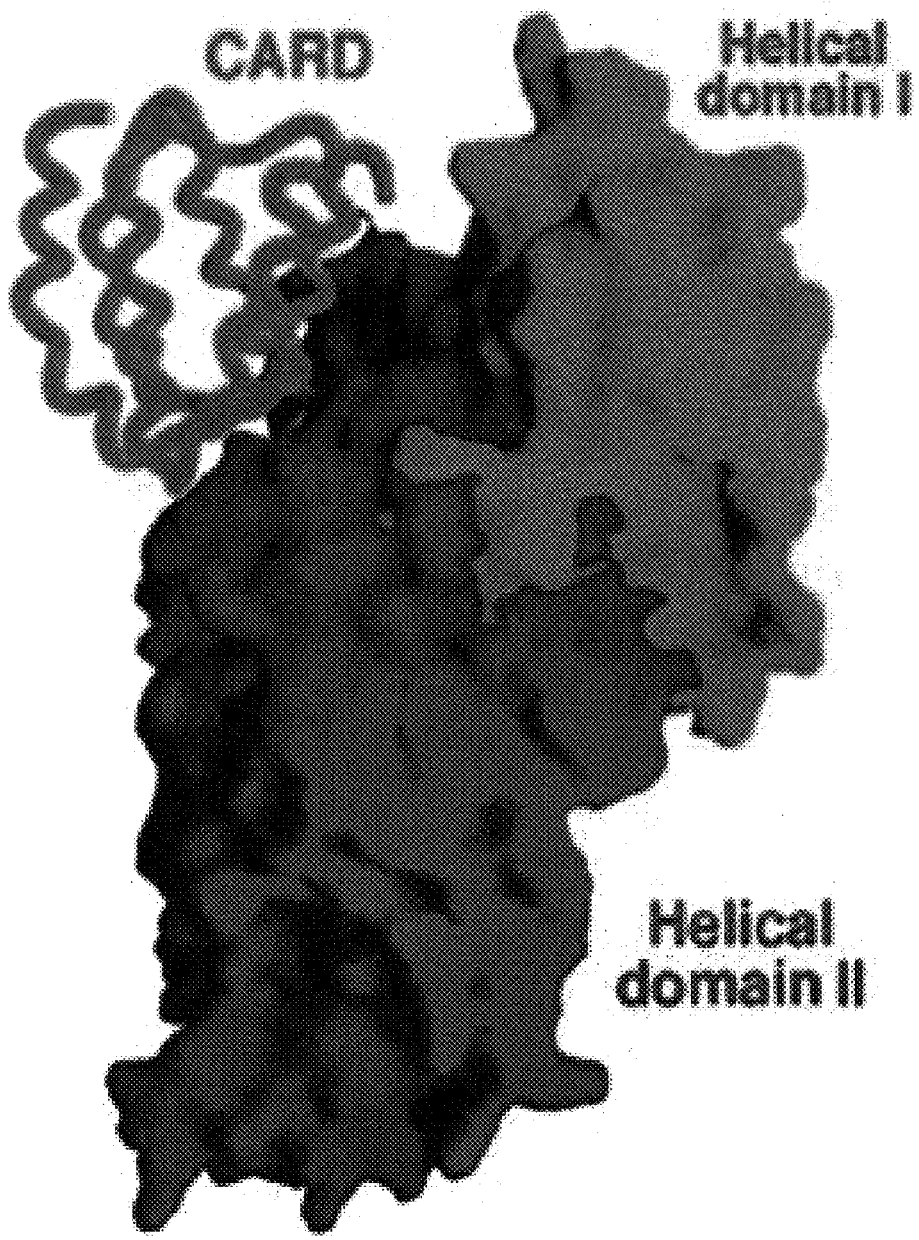
FIG. 2C is a surface representation of the Apaf-1 fragment shown in FIG. 2B.

A ribbon plot of the three-dimensional structure of the soluble Apaf-1 fragment (i.e., residues 1-591 of full length Apaf-1) is shown in FIG. 2. The structure reveals five distinct domains that pack against each other through extensive intramolecular interactions. Those domains are shown in FIGS. 2 and 3.

The N-terminal CARD domain (residues 1-107; colored green in FIGS. 2 and 3) comprises six alpha helices, alpha1 through alpha6, arranged in a Greek key topology. The structure of CARD in the context of other Apaf-1 domains is identical to that of the isolated CARD domain (Qin et al., 1999, Nature 399:547-555; Vaughn et al., 1999, J. Mol. Biol. 293:439-447; Zhou et al., 1999, Proc. Natl. Acad. Sci. USA 96:11265-11270).

The alpha/beta fold domain (residues 108-284; colored blue in FIGS. 2 and 3) consists of five parallel beta strands, beta1-beta5, in the center, sandwiched by four alpha helices on either side.

A short alpha-helical domain (helical domain I, residues 285-365; colored cyan in FIGS. 2 and 3), containing four alpha helices, alpha16-alpha19, is followed by a winged-helix domain (residues 366-450; colored magenta in FIGS. 2 and 3). Occurrence of a winged-helix domain was considered unexpected, because such domains usually occur in eukaryotic transcription factors (Kaufmann et al., 1996, Mech. Dev. 57:3-20).

The C-terminal extended domain (helical domain II, residues 451-591; colored red in FIGS. 2 and 3) is composed of exclusively alpha helices, alpha26-alpha32, arranged in a left-handed, super-helical conformation.

The centrally located winged-helix domain is capped by the alpha/beta fold domain and helical domain I on the top, helical domain II at the bottom, and CARD on the side. Together, these five domains give rise to a relatively compact structure, having a length of about 80 Angstroms, a width of about 55 Angstroms, and a thickness of about 65 Angstroms. ADP is bound at the interface between three domains: the alpha/beta fold, helical domain I, and the winged-helix domain. Strikingly, the bound ADP molecule is deeply buried and inaccessible to even small molecules unless the conformation is changed. The inaccessible nature of the nucleotide-binding site indicates that the structure of Apaf-1 bound to ADP is in a closed conformation, unable to activate caspase-9 until opened.

To facilitate structural analysis, an internet-based search for structural homologues of Apaf-1 was performed using the program DALI (Holm et al., 1993, J. Mol. Biol. 233:123-138). Two of the most homologous structures were found to be the hexamerization D2 domain of n-ethylmaleimide-sensitive fusion protein (NSF), which is an essential ATPase required for intracellular vesicle fusion (Lenzen et al., 1998, Cell 94:525-536), and p97 (Zhang et al., 2000, Mol. Cell 6:1473-1484).

Both NSF and p97 belong to the AAA (ATPases associated with various cellular activities) family of ATPases (Lupas et al., 2002, Curr. Opin. Struct. Biol. 12:746-753). The conserved regions encompass the entire alpha/beta fold and helical domain I, with a root-mean-square deviation (RMSD) of approximately 4.7 Angstroms over 201 aligned C-alpha atoms between Apaf-1 and NSF or 4.4 Angstroms over 198 C-alpha atoms between Apaf-1 and p97. The presence of a short helical domain following the alpha/beta fold is a hallmark of the AAA family of ATPases, in which the helical domain energetically contributes to nucleotide binding (Lupas et al., 2002, Curr. Opin. Struct. Biol. 12:746-753). This analysis, in conjunction with sequence features identifiable in FIG. 3, indicates that Apaf-1 belongs to the AAA+ family of ATPases.

CARD in a Closed Conformation

Figure 4A:
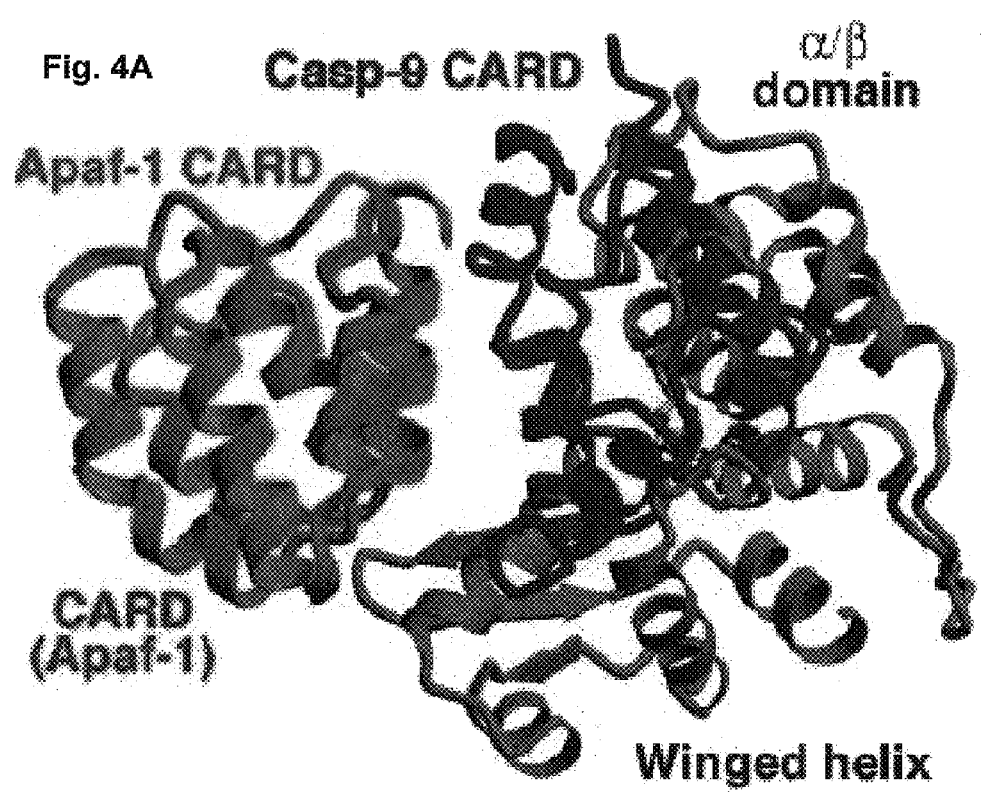
FIG. 4A is a ribbon plot showing that the CARD domain of the ADP-bound Apaf-1 (shown in green in this figure) exists in a closed conformation, because this conformation does not allow the CARD domain of Apaf-1 to interact with the prodomain of caspase-9 (shown in pink in this figure). To demonstrate this point, the prodomain of caspase-9 was docked onto the CARD domain of the ADP-bound Apaf-1 on the basis of previously determined structure of the complex between the isolated Apaf-1 CARD (shown in cyan in this figure) and the caspase-9 prodomain. Severe steric clash exists between the prodomain of caspase-9 and the alpha/beta fold and winged-helix domains of Apaf-1 (each shown in grey in this figure).

The CARD domain of Apaf-1 interacts with the prodomain of caspase-9 and this interaction is essential for the recruitment and subsequent activation of caspase-9 (Li et al., 1997, Cell 91:479-489; Qin et al., 1999, Nature 399:547-555). In the Apaf-1 structure, the N-terminal CARD domain stacks closely against the alpha/beta fold and the winged-helix domain through a large interface involving helices alpha2, alpha4, and alpha5 of the CARD domain, as shown in FIG. 4.

Helix alpha2 of the Apaf-1 CARD domain is required for binding to the prodomain of caspase-9 (Qin et al., 1999, Nature 399:547-555; Zhou et al., 1999, Proc. Natl. Acad. Sci. USA 96:11265-11270). Simulated docking of caspase-9 prodomain to the CARD domain of Apaf-1 indicated significant steric clash between caspase-9 prodomain and the alpha/beta fold of Apaf-1.

Thus, in order for Apaf-1 to interact with caspase-9, the relative orientation of CARD with respect to the rest of Apaf-1 structure must be changed. In addition, the packing of CARD with other domains of Apaf-1 further restricts access to the bound ADP molecule (e.g., see FIGS. 4B and 4C). This structural analysis further indicates that ADP-bound Apaf-1 adopts a closed conformation and that exchange and/or hydrolysis of nucleotide is likely to affect the interaction of CARD with other domains of Apaf-1. The observation by Li et al. Cell 91:479-489) that caspase-9 efficiently binds to full-length Apaf-1 only in the presence of cytochrome c and dATP/ATP is in agreement with this analysis.

Figure 4C:
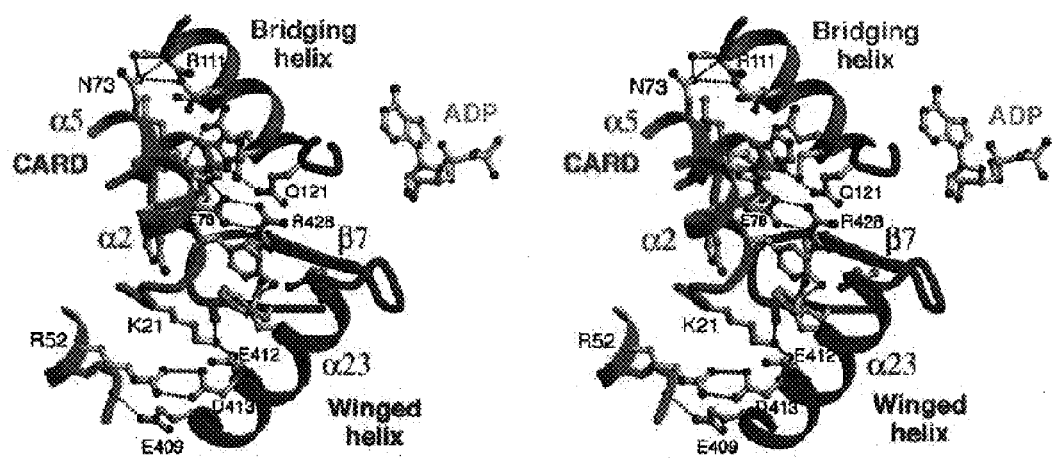
FIG. 4C is a stereoscopic view of the specific interactions between the CARD domain and the alpha/beta fold and the winged-helix domains. Colors are as in FIG. 4B. Hydrogen bonds are represented by red dashed lines. ADP is shown to indicate the topology of CARD packing and ADP binding.

The interactions between CARD and the alpha/beta fold and the winged-helix domain primarily involve a network of 13 inter-domain hydrogen bonds, with limited van der Waals contacts (as shown in FIG. 4C). Approximately half of the interactions with CARD are mediated by residues from the alpha/beta fold, with the bridging helix (alpha8) contributing the bulk; the other half comes from strands beta7/beta8 and helix alpha23 of the winged-helix domain. At one end of the interface, the bridging helix alpha8, though not conserved in other alpha/beta fold domains, mediates four hydrogen bonds and several van der Waals contacts. In the center of this interface, Glu78 of the CARD domain makes a bifurcated hydrogen bond to Arg428 of the winged helix domain. This interaction is buttressed on either end by one inter-domain hydrogen bond and a few van der Waals contacts. At the other end of the interface, Arg52 of the CARD domain donates two specific hydrogen bonds to the carboxylate group of Asp413 on the winged-helix domain, which is reinforced by three additional inter-domain hydrogen bonds.

The extensive inter-domain packing results in the burial of an approximately 2550 square Angstrom solvent-exposed surface area between CARD and the alpha/beta fold and the winged-helix domain. These CARD-mediated interactions are dominated by hydrogen bonds, which are conducive to regulation due to their fast kinetic rates. In addition, these interactions appear to significantly stabilize the limited contact between the alpha/beta fold and the more C-terminal winged-helix domain, allowing His438 of the winged-helix domain to make a direct hydrogen bond to stabilize the bound ADP molecule (see FIG. 5). Ser422 of the winged-helix domain donates another water-mediated hydrogen bond to the ribose ring of ADP. These observations indicate that an inter-domain rearrangement, induced by binding and/or hydrolysis of ATP, can result in the loss of inter-domain interactions involving the CARD domain, thus destabilizing the limited contact between the alpha/beta fold and the winged-helix domain and converting Apaf-1 into a conformation in which it can activate caspase-9. In contrast to known structures of the AAA ATPases, the winged-helix domain of Apaf-1 is involved in coordinating ADP and hence blocks access to the nucleotide-binding pocket. This unique structural feature suggests that the winged-helix domain undergoes a large-scale conformational shift upon exchange/hydrolysis of nucleotide.

Effect of Caspase Binding to CARD

To examine whether CARD in the closed conformation of Apaf-1 is capable of binding to caspase-9, we incubated the soluble Apaf-1 fragment (i.e., residues 1-591 of full length Apaf-1) with the full length, processed caspase-9 (residues 1-416) and compared the behavior of the complex with either component on gel filtration chromatography. The elution volume for Apaf-1 (residues 1-591) corresponds to a molecular mass of a monomer (i.e., 65 kilodaltons). The elution volume for caspase-9, which contains an extended linker segment between its prodomain and the caspase unit, corresponds to a molecular mass of about 90 kilodaltons, almost twice of that expected for a monomer (47 kilodaltons). This discrepancy is likely caused by the enlarged radius of hydration of caspase-9 due to the extended linker segment, because caspase-9 exists exclusively as a monomer in solution. When equi-molar amounts of Apaf-1 and caspase-9 were used, the center of the protein peak was shifted to an earlier fraction, which corresponds to a molecular mass of approximately 130 kilodaltons, consistent with a 1:1 complex between Apaf-1 and caspase-9. The formation of the Apaf-1/caspase-9 complex appeared to be inefficient, as judged by trailing fractions that likely contained non-interacting Apaf-1 or caspase-9.

Next, we investigated whether formation of a 1:1 complex between Apaf-1 and caspase-9 had any effect on the catalytic activity of caspase-9. Surprisingly, the activity of caspase-9 was significantly and reproducibly elevated in the presence of Apaf-1 despite the absence of ATP and the absence of the apoptosome. This observation suggests that, even in a 1:1 complex, Apaf-1 is able to allosterically enhance the catalytic activity of caspase-9. The formation of the apoptosome can greatly accelerate this process.

Nucleotide Binding

A surprising revelation of the Apaf-1 structure is that the bound nucleotide is ADP rather than ATP. The binding pocket for ADP is formed at the junction of four domains, CARD, alpha/beta fold, helical domain I, and winged-helix domain. ADP binding appears to help bring together these adjoining four domains. Consequently, the bound ADP molecule is buried and the only narrow channel from ADP to solvent is blocked by the packing of the CARD domain. This structural organization strongly indicates that unpacking of CARD, which can be achieved through interaction with the prodomain of caspase-9, leads to a more accessible nucleotide binding pocket.

Consistent with this analysis, dATP/ATP binding to Apaf-1 was shown by Jiang et al. (2000, J. Biol. Chem. 275:31199-

31203) to be facilitated by the presence of caspase-9. Our structural analysis also suggests that even a slight perturbation to the nucleotide-binding pocket, such as exchange or hydrolysis of nucleotide, may result in the disruption of the inter-domain packing among the four adjoining subunits. This suggests that nucleotide analogs can significantly modulate the activity of Apaf-1, either enhancing or inhibiting the activity, depending on the effect of the particular analog on interactions between the subunits. The structure of Apaf-1 described herein indicates the types and structures of ADP/dADP/ATP/dATP analogs that can be expected to modulate Apaf-1 activity.

Figure 5:
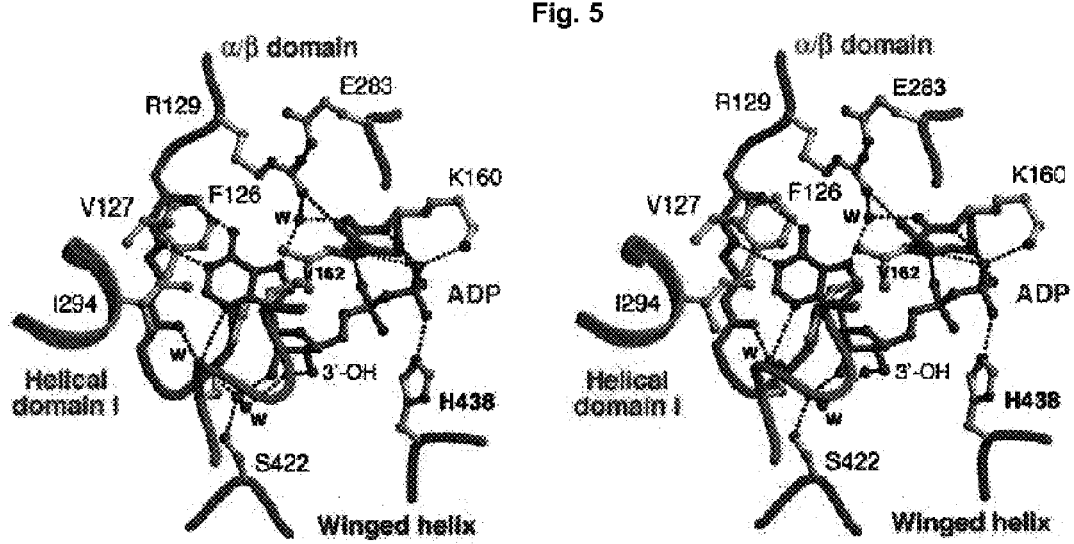
FIG. 5 is a stereoscopic representation of the coordination of ADP by residues from three domains of Apaf-1. Similar to other AAA ATPases, ADP is primarily bound to the hinge region between the alpha/beta fold (blue) and helical domain I (cyan). Yet the winged-helix domain (pink) also contributes a direct hydrogen bond to the beta-phosphate group (from His438) and a water-mediated hydrogen bond to the ribose (from Ser422).

The adenine base of the bound ADP exists in the anti conformation with respect to the ribose (see FIG. 5). The specific binding of ADP is achieved by a total of eight direct hydrogen bonds from residues in Apaf-1, including two to the adenine base and six to the phosphate groups. The main chain carbonyl and amide groups of Val127 from the alpha/beta fold form hydrogen bonds to the N6 and N1 atoms of the adenine base, respectively. These two hydrogen bonds are specific for the adenine but not the guanine base, explaining why GTP does not activate Apaf-1, as others have observed (e.g., Li et al., 1997, Cell 91:479-489). The alpha-phosphate is coordinated through only one hydrogen bond by the amide group of Val 162. In contrast, the beta-phosphate is coordinated by five hydrogen bonds, from the amide groups of Gly159, Lys160 and Ser161, the side chain amino group of Lys160 and the imidazole group of His438. Gly159, Lys160, Ser161 and Val162 come from the P-loop (also known as Walker A motif) of the alpha/beta fold whereas His438 is located within the winged-helix domain.

A few well-ordered water molecules appear to play an important role in binding to ADP. The side chain of Arg129 and the carbonyl group of Gly159 make a water-mediated hydrogen bond to the N7 atom of the adenine base; whereas Val125 and Ser422 make water-mediated hydrogen bonds to the adenine base and the ribose, respectively (see FIG. 5). In addition to hydrogen bonds, a number of residues stabilize the adenine and the ribose moieties through van der Waals contact, including Pro123, Phe126, Val127, Arg129, Gly159 and Val162 from the alpha/beta fold, and Ile294, Pro321, Leu322 and Ser325 from helical domain I. These and other features indicate suitable structures for adenine nucleotide analogs for modulating Apaf-1 activity.

Compared to other members of the AAA+ ATPase family, the unique feature of Apaf-1 is the involvement of the winged-helix domain in the coordination of ADP, with His438 and Ser422 contributing two hydrogen bonds. Consequently, the ADP molecule is deeply buried. The significant yet weak interactions between ADP and the winged-helix domain suggests that this domain may be prone to conformational shifts.

ATP Hydrolysis

Both structural comparison with other AAA ATPases such as p97 (Zhang et al., 2000, Mol. Cell 6:1473-1484) and sequence features indicate that Apaf-1 belong to the AAA+ family of ATPase (Neuwald et al., 1999, Genome Res. 9:27-43), consistent with an earlier suggestion (Jaroszewski et al., 2000, Proteins 39:197-203). The sequences of Apaf-1 contain all the key elements of an ATPase that are required for activity, including the P-loop and the Walker B motif. However, whether Apaf-1 is a bona fide ATPase remained unresolved, largely due to the technical difficulty in eliminating trace amounts of contaminating ATPases (Zou et al., 1999, J. Biol. Chem. 274:11549-11556; Saleh et al., 1999, J. Biol. Chem. 274:17941-17945; Jiang et al., 2000, J. Biol. Chem. 275:31199-31203). It was also unknown whether ATP hydrolysis is essential to the function of Apaf-1 and, if so, how ATPase activity is related to the function of Apaf-1.

To definitively address these issues, we over-expressed the soluble Apaf-1 fragment (residues 1-591) described in this example in *E. coli* and purified this recombinant protein to homogeneity. Unlike full-length Apaf-1 that was expressed and purified from baculovirus-infected insect cells, the bacteria-derived Apaf-1 is free of any detectable contaminating proteins as judged by SDS-PAGE, amino acid analysis, HPLC, and mass spectroscopy. This Apaf-1 protein fragment is folded well, as judged by gel filtration and circular dichroism analyses.

Using thin layer chromatography (TLC), we reconstituted an in vitro ATPase assay to detect the hydrolysis of (alpha-$^{32}$P)-labeled ATP, and raw results obtained using this assay method are shown in FIG. 6A. The recombinant Apaf-1 protein, but not caspase-9, exhibited ATPase activity, as evidenced by the appearance of ADP on TLC (FIG. 6A, lanes 1 & 2). Incubation of this reaction with EDTA resulted in the abrogation of the observed ATPase activity (lane 3), owing to removal of magnesium ion that is required for ATP hydrolysis. Supplementation with magnesium in excess of EDTA restored the ATPase activity (lane 4). In addition, Apaf-1 exhibited a similar level of ATPase activity in the presence of caspase-9 (lanes 5-7). These results show unambiguously that Apaf-1 is capable of hydrolyzing ATP and this activity is dependent upon the presence of magnesium ion.

Figure 6C:
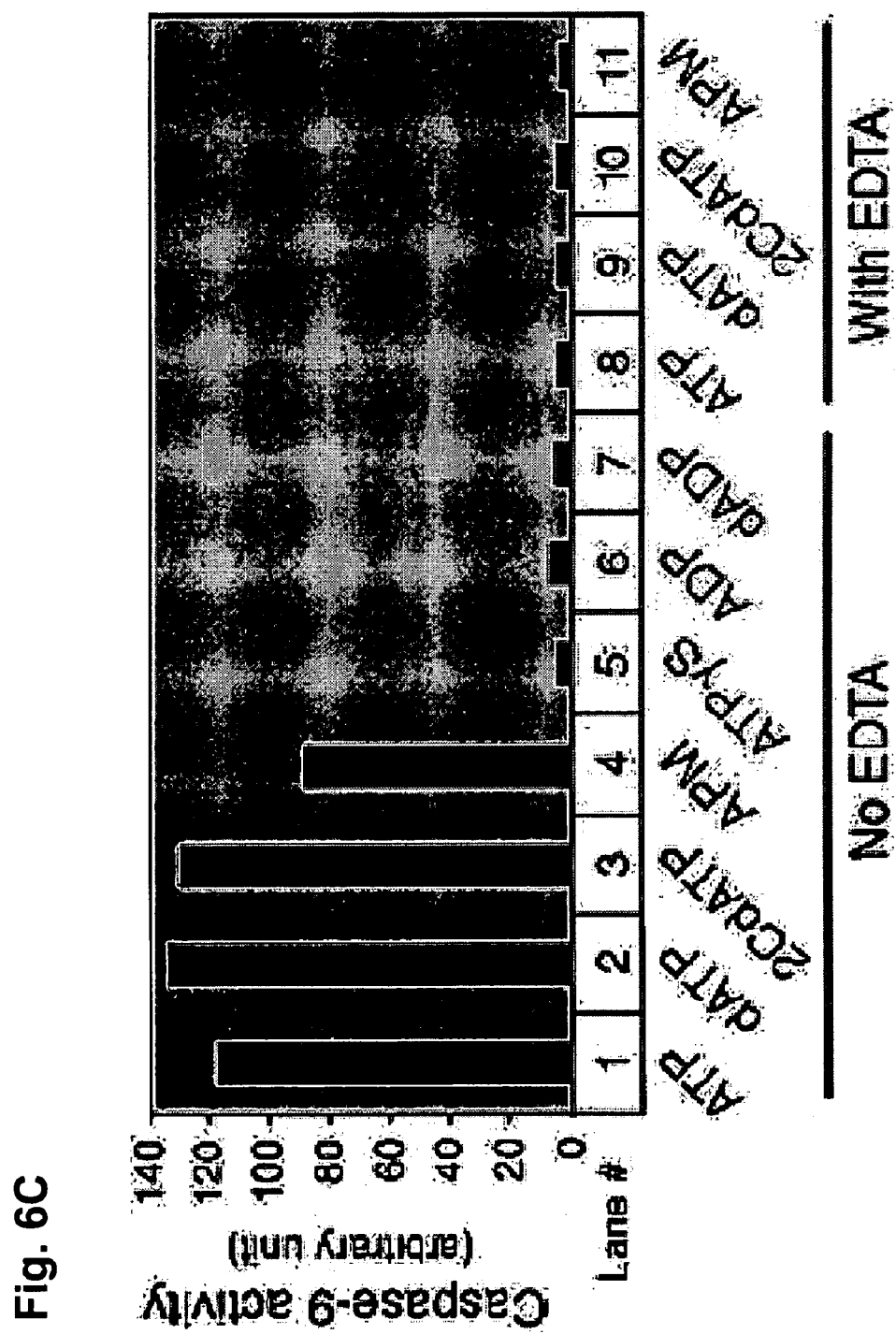

Next, we examined whether ATPase activity is essential to the function of Apaf-1 using an in vitro reconstituted caspase-9 activation assay. These results are shown in FIG. 6B. The activation of caspase-9 refers to the apoptosome-mediated enhancement of caspase-9 activity in the apoptosome holoenzyme, where the proteolytic activity of caspase-9 can be elevated by two- to three-orders of magnitude compared to the isolated caspase-9 (Rodriguez et al., 1999, Genes Dev. 13:3179-3184). As anticipated, the proteolytic activity of the isolated caspase-9 remains low (FIG. 6B, lane 1). Incubation of caspase-9 with Apaf-1 significantly improved the caspase catalytic activity (lane 2); the addition of ATP further drastically improved caspase-9 activity (lane 3), confirming the critical function of ATP binding. Importantly, eliminating ATPase activity through the use of EDTA completely abolished the positive effect of ATP (lane 4), strongly indicating that ATP hydrolysis is essential to Apaf-1-mediated activation of caspase-9. To further confirm this conclusion, ATPase assays were performed for these proteins under identical conditions and the results correlated with caspase-9 activation.

dATP has been reported to be a more potent activator of the apoptosome-mediated caspase-9 activation than ATP (Li et al., 1997, Cell 91:479-489). At a concentration of 2 micromolar, dATP promoted greater activation of caspase-9 than did ATP. We also discovered that, in contrast to ATP, dATP exhibits an optimal range of concentration at 1-5 micromolar. At higher concentrations of dATP, Apaf-1-mediated activation of caspase-9 is reduced slightly. Similar to ATP, dATP-mediated activation is dependent on its hydrolysis, because blocking the ATPase activity of Apaf-1 in the presence of 1 millimolar EDTA and 2 micromolar dATP also completely abolished caspase-9 activation (e.g., compare FIG. 6C, lanes 2 and 9). Finally, the essential requirement of ATP/dATP hydrolysis for caspase-9 activation was further confirmed by the use of ATP-gamma-S, which was unable to support caspase-9 activation (FIG. 6C, lane 5).

Effect of Nucleotide Analogs

The dATP analog 2-chloro-deoxyadenosine (2CdA) is an effective agent in the treatment of several forms of cancer such as chronic lymphocytic leukemia (CLL) and hairy cell leukemia (Juliusson et al., 1996, J. Clin. Oncol. 14:2160-2166). The cytotoxicity of 2CdA largely depends on the accumulation of its 5'-triphosphate metabolite 2CdATP (Juliusson et al., 1996, J. Clin. Oncol. 14:2160-2166; Kawasaki et al., 1993, Blood 81:597-601). The chemotherapeutic effect of 2CdATP cannot be completely attributed to its deleterious incorporation into newly synthesized DNA, because 2CdATP also induces apoptosis in non-dividing lymphocytes (Juliusson et al., 1996, J. Clin. Oncol. 14:2160-2166). Interestingly, 2CdATP was shown to cooperate with cytochrome c and Apaf-1 to activate caspase-3 in a cell-free system (Leoni et al., 1998, Proc. Natl. Acad. Sci. USA 95:9567-9571; Genini et al., 2000, J. Biol. Chem. 275:29-34).

To further investigate the molecular mechanism by which 2CdATP regulates the function of Apaf-1, we examined the effect of various concentrations of 2CdATP on caspase-9 activation. As anticipated, 2CdATP is a potent activator for caspase-9 activation, with an optimal working concentration of approximately 100 micromolar. Similar to ATP and dATP, the hydrolysis of 2CdATP by Apaf-1 is essential to caspase-9 activation, as EDTA incubation led to loss of this response (compare FIG. 6C, lanes 3 and 10). In addition, another ATP analog, 2-methylthio-ATP (APM), also supported Apaf-1-mediated caspase-9 activation and inhibition of its hydrolysis abrogated this effect (compare FIG. 6C, lanes 4 and 11).

In the ADP-binding site of Apaf-1, the adenine- and ribose-binding pocket contains five well-ordered water molecules, which mediate hydrogen bonds between ADP and amino acid residues from Apaf-1 (see FIG. 5). This structural observation indicates that small polar groups can be incorporated into the adenine and ribose moieties of ATP or dATP to generate nucleotide analogs that may bind to Apaf-1 with much higher affinity. Because the binding affinity of a nucleotide or nucleotide analog correlates with its ability to induce caspase-9 activation, synthesis of novel nucleotide analogs that bind to Apaf-1 with higher affinity is expected to enhance the ability of such analogs to induce apoptosis in cancer cells.

Implications on Apoptosome Assembly

The role of ATP hydrolysis is manifest from the structural analysis presented in this example: hydrolysis of ATP at the junction of four subunits results in the reorganization of these domains and subsequent formation of the apoptosome. Indeed, the AAA+ family of proteins, such as the large T antigen of the DNA tumor virus SV40, is known to couple ATP hydrolysis with conformational changes that result in important functional consequences (Gai et al., 2004, Cell 119:47-60; Gai et al., 2004, J. Biol. Chem. 279:38952-38959; Wang, 2004, J. Struct. Biol. 148:259-267).

In order to identify conformational changes to Apaf-1 that ATP hydrolysis brings about, we studied known AAA+ ATPases and observed that their oligomerization (frequently hexamerization) is mediated by a conserved mode of domain organization. For example, for both NSF and p97, the far end of the alpha/beta fold of one protomer stacks against the wedge between the alpha/beta fold and its carboxyl-terminal helical domain of the adjacent protomer. This interaction is repeated six times, resulting in the hexamerization of NSF. The same general interface topology was also observed in a number of other AAA+ ATPases, including the bacterial protein HslU and the viral protein SV40 large T antigen. Thus the overall packing arrangement at the oligomerization interface of AAA+ ATPases is conserved.

The ADP-bound Apaf-1 exists in a closed conformation. In agreement with the biochemical and structural analysis presented herein, superposition of the alpha/beta fold of Apaf-1 into that of one NSF protomer in the hexameric structure results in extensive overlap of structures among neighboring Apaf-1 molecules. To remove these severe steric clash, the winged-helix domain and helical domain II must be dislocated from their current positions and rotated by approximately 45-50 degrees. This re-organization allows the formation of a symmetric oligomer for Apaf-1 (FIG. 7), which closely resembles the core of the 27 Angstrom structure of the apoptosome generated by cryo-electron microscopy (Acehan et al., 2002, Mol. Cell 9:423-432). It should be noted that, although hexameric symmetry is presented in FIG. 7 for Apaf-1, heptameric symmetry can be obtained by a very small degree of rotation (about 8.5 degrees) between two neighboring protomers of Apaf-1, which may not significantly disrupt their packing interactions.

The proposed conformational change in Apaf-1 is supported by all available structural, biochemical, and sequence information. First, the structural organization of the four subunits at the ADP-binding site strongly suggests an ATP hydrolysis-induced conformational change. His438 from the winged-helix domain directly coordinates the beta-phosphate of ADP. Second, biochemical characterization indicates that ATP hydrolysis is coupled to apoptosome formation and subsequent caspase-9 activation. Third, Apaf-1 shares significant structural homology with the hexamerization domain of NSF and p97, suggesting a similar mode of oligomerization. More importantly, the interface organization of the AAA+ family of proteins appears to be conserved, allowing us to predict conformational changes in Apaf-1 based on known structures.

In this example, the crystal structure of Apaf-1 bound to ADP at 2.2-Angstrom resolution has been described. In the structure, ADP is located at the junction of and coordinated by four domains. Binding to ADP has an essential role in organizing the structure of Apaf-1 into a closed form, in which the CARD domain packs against three other subunits and the ATPase domain exhibits a conformation that is incompatible with formation of the apoptosome.

The full activation of caspase-9 appears to comprise two stages. In the first stage, Apaf-1-mediated binding of caspase-9 in the absence of ATP/dATP leads to significant elevation of the caspase-9 activity. This observation indicates that monomeric Apaf-1 can allosterically improve caspase-9 activity, either through direct modification of the caspase-9 active site or by relieving the negative impact of caspase-9 prodomain on its own catalytic activity (Shi, 2004, Cell in press).

In the second stage, binding and hydrolysis of ATP/dATP induces a conformational change in Apaf-1 that propels its oligomerization and formation of the apoptosome holoenzyme. This reorganization depends on the energy released by the hydrolysis of bound nucleotide. Importantly, nucleotide analogs such as 2CdATP can also substitute ATP/dATP to activate Apaf-1. The binding of such nucleotide analogs is safeguarded by the enlarged ADP-binding pocket, which further suggests synthetic approach to improve the binding affinity and hence potency of the nucleotide analogs. Such analogs have important uses the therapeutic treatment of cancer, for instance.

TABLE I

Diffraction data and refinement statistics.

| | Data set | | | |
|---|---|---|---|---|
| | Native | Hg (inflection) | Hg (remote) | Hg (peak) |
| Source | CHESS A-1 | NSLS - X25 | NSLS - X25 | NSLS - X25 |
| Wavelength (Angstrom) | 0.954 | 1.0088 | 0.9500 | 1.0053 |
| Resolution range (Angstroms) | 50.0-2.2 | 50.0-2.8 | 50.0-2.8 | 50.0-2.8 |
| Space group | P1 | $P2_1$ | $P2_1$ | $P2_1$ |
| Unit cell P1 | a = 75.96 Angstroms, b = 92.88 Angstroms, c = 94.99 Angstroms, alpha = 62.96 degrees, beta = 89.99 degrees, gamma = 90.05 degrees | | | |
| Unit cell $P2_1$ | a = 47.83 Angstroms, b = 76.01 Angstroms, c = 81.15 Angstroms, beta = 91.33 degrees | | | |
| Reflections observed | 174,841 | 49,104 | 49,202 | 47,562 |
| Reflections unique | 103,300 | 14,241 | 14,340 | 13,998 |
| Completeness (%) (last shell) | 89.5 (48.9) | 97.9 (95.2) | 98.5 (93.9) | 96.2 (94.6) |
| I/σ (last shell) | 12.7 (2.5) | 12.3 (2.7) | 12.5 (2.9) | 11.3 (1.7) |
| $R_{merge}^a$ (%) (last shell) | 4.8 (26.7) | 8.3 (47.7) | 8.1 (45.0) | 9.7 (70.3) |

| Phasing | |
|---|---|
| Resolution range (Angstroms) | 50.0-3.1 |
| Hg sites | 6 |
| FOM from Solve/Resolve | 0.49/0.66 |
| Refinement statistics | |
| Resolution range (Angstroms) | 15.00-2.21 |
| Reflections (total) | 102,922 |
| $R_{cryst}^b / R_{free}^c$ (%) | 18.93/24.37 |
| Protein residues/atoms | 2,322/18,656 |
| ADP molecules/atoms | 4/108 |
| Water molecules | 782 |
| RMSD angles (degrees) | 1.43 |
| RMSD bonds (Angstrom) | 0.013 |
| Average isotropic B-value | 36.3 square Angstroms |

$^a R_{merge} = \Sigma |I - <I>|/\Sigma I$, where I is the observed intensity and <I> is the average intensity from multiple observations of symmetry-related reflections, the value in parentheses correspond to the highest resolution shell.
$^b R_{cryst} = \Sigma |(F_{obs}) - (F_{calc})|/\Sigma(F_{obs})$,
$^c R_{free}$ = same as $R_{cryst}$ but comprises a test set (5.1% total Reflections), which was not used in model refinement.

TABLE 2

Expression and Solubility of Apaf-1 Fragments in E. coli

| Fragment of SEQ ID NO: 1 | Amino Acid Modification(s) | Expression | Solubility |
|---|---|---|---|
| (Full Length Apaf-1) | | – | – |
| 1-286 | | +++ | +/– |
| 1-349 | | ++++ | ++ |
| 1-469 | | +++ | + |
| 1-554 | | +++ | ++ |
| 1-567 | | +++ | +++ |
| 1-570 | | +++ | +++ |
| 1-589 | | ++++ | ++++ |
| 1-589 | C568S | ++++ | ++++ |
| 1-589 | C568S, C115S | ++++ | ++++ |
| 1-591 | | ++++ | ++++ |
| 1-591 | K160R | ++ | ++ |
| 1-591 | C568S, C115S | ++++ | ++++ |
| 94-591 | | ++ | ++ |
| 572-end of full length Apaf-1 | | ++ | – |
| 588-end of full length Apaf-1 | | ND | – |

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. An isolated soluble, functional fragment of a metazoan apoptotic protease-activating factor 1 (Apaf-1), the fragment having an amino acid sequence that comprises residues 94-349 of SEQ ID NO: 1 and lacking a portion of the WD40 repeat domain of the factor, wherein the native full-length amino acid sequence of the factor comprises SEQ ID NO: 1.

2. The fragment of claim 1, wherein the factor is Apaf-1 of a chordate.

3. The fragment of claim 1, wherein the factor is human Apaf-1.

4. The fragment of claim 1, wherein the cysteine residue present at residue 115 of SEQ ID NO: 1 is altered to be a serine residue.

5. The fragment of claim 1, wherein the lysine residue present at residue 160 of SEQ ID NO: 1 is altered to be an arginine residue.

6. The fragment of claim 1, having an amino acid sequence that comprises residues 1-349 of SEQ ID NO: 1.

7. The fragment of claim 1, having an amino acid sequence that comprises residues 94-589 of SEQ ID NO: 1.

8. The fragment of claim 7, wherein the cysteine residue present at residue 568 of SEQ ID NO: 1 is altered to be a serine residue.

9. The fragment of claim 1, having an amino acid sequence that comprises residues 1-591 of SEQ ID NO: 1.

10. The fragment of claim 1, comprising most of the helical domain I of the factor.

11. The fragment of claim 1, further comprising the CARD domain of the factor.

12. The fragment of claim 1, further comprising the winged-helix domain of the factor.

13. The fragment of claim 12, further comprising at least most of the helical domain II of the factor.

14. The fragment of claim 1, comprising the entire helical domain I of the factor and further comprising the CARD domain, the winged-helix domain, and most of the helical domain II of the factor.

15. The fragment of claim 14, comprising the entire helical domain II and at least a portion of the WD40 repeat domain of the factor.

* * * * *

SEQUENCE LISTING

<160> NUMBER OF SEQ ID NOS: 8

<210> SEQ ID NO 1
<211> LENGTH: 591
<212> TYPE: PRT
<213> ORGANISM: Homo sapiens

<400> SEQUENCE: 1

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Val Phe Val Thr
        115                 120                 125

Arg Lys Lys Leu Val Asn Ala Ile Gln Gln Lys Leu Ser Lys Leu Lys
    130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
                165                 170                 175

Cys Phe Pro Gly Gly Val His Trp Val Ser Val Gly Lys Gln Asp Lys
            180                 185                 190

Ser Gly Leu Leu Met Lys Leu Gln Asn Leu Cys Thr Arg Leu Asp Gln
        195                 200                 205

Asp Glu Ser Phe Ser Gln Arg Leu Pro Leu Asn Ile Glu Glu Ala Lys
    210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
                245                 250                 255

Gln Cys Gln Ile Leu Leu Thr Thr Arg Asp Lys Ser Val Thr Asp Ser
            260                 265                 270

Val Met Gly Pro Lys Tyr Val Val Pro Val Glu Ser Ser Leu Gly Lys
        275                 280                 285

Glu Lys Gly Leu Glu Ile Leu Ser Leu Phe Val Asn Met Lys Lys Ala
    290                 295                 300

Asp Leu Pro Glu Gln Ala His Ser Ile Ile Lys Glu Cys Lys Gly Ser
305                 310                 315                 320

Pro Leu Val Val Ser Leu Ile Gly Ala Leu Leu Arg Asp Phe Pro Asn
                325                 330                 335

Arg Trp Glu Tyr Tyr Leu Lys Gln Leu Gln Asn Lys Gln Phe Lys Arg
            340                 345                 350

Ile Arg Lys Ser Ser Ser Tyr Asp Tyr Glu Ala Leu Asp Glu Ala Met

```
              355                 360                 365
Ser Ile Ser Val Glu Met Leu Arg Glu Asp Ile Lys Asp Tyr Tyr Thr
        370                 375                 380

Asp Leu Ser Ile Leu Gln Lys Asp Val Lys Val Pro Thr Lys Val Leu
385                 390                 395                 400

Cys Ile Leu Trp Asp Met Glu Thr Glu Glu Val Glu Asp Ile Leu Gln
                405                 410                 415

Glu Phe Val Asn Lys Ser Leu Leu Phe Cys Asp Arg Asn Gly Lys Ser
            420                 425                 430

Phe Arg Tyr Tyr Leu His Asp Leu Gln Val Asp Phe Leu Thr Glu Lys
        435                 440                 445

Asn Cys Ser Gln Leu Gln Asp Leu His Lys Lys Ile Ile Thr Gln Phe
    450                 455                 460

Gln Arg Tyr His Gln Pro His Thr Leu Ser Pro Asp Gln Glu Asp Cys
465                 470                 475                 480

Met Tyr Trp Tyr Asn Phe Leu Ala Tyr His Met Ala Ser Ala Lys Met
                485                 490                 495

His Lys Glu Leu Cys Ala Leu Met Phe Ser Leu Asp Trp Ile Lys Ala
            500                 505                 510

Lys Thr Glu Leu Val Gly Pro Ala His Leu Ile His Glu Phe Val Glu
        515                 520                 525

Tyr Arg His Ile Leu Asp Glu Lys Asp Cys Ala Val Ser Glu Asn Phe
    530                 535                 540

Gln Glu Phe Leu Ser Leu Asn Gly His Leu Leu Gly Arg Gln Pro Phe
545                 550                 555                 560

Pro Asn Ile Val Gln Leu Gly Leu Cys Glu Pro Glu Thr Ser Glu Val
                565                 570                 575

Tyr Gln Gln Ala Lys Leu Gln Ala Lys Gln Glu Val Asp Asn Gly
            580                 585                 590

<210> SEQ ID NO 2
<211> LENGTH: 1194
<212> TYPE: PRT
<213> ORGANISM: Homo sapiens

<400> SEQUENCE: 2

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Val Arg Thr Val Leu Cys Glu Gly Gly Val Pro Gln Arg Pro
            100                 105                 110

Val Val Phe Val Thr Arg Lys Lys Leu Val Asn Ala Ile Gln Gln Lys
        115                 120                 125

Leu Ser Lys Leu Lys Gly Glu Pro Gly Trp Val Thr Ile His Gly Met
    130                 135                 140
```

```
Ala Gly Cys Gly Lys Ser Val Leu Ala Ala Glu Ala Val Arg Asp His
145                 150                 155                 160

Ser Leu Leu Glu Gly Cys Phe Pro Gly Gly Val His Trp Val Ser Val
            165                 170                 175

Gly Lys Gln Asp Lys Ser Gly Leu Leu Met Lys Leu Asn Leu Cys
        180                 185                 190

Thr Arg Leu Asp Gln Asp Glu Ser Phe Ser Gln Arg Leu Pro Leu Asn
    195                 200                 205

Ile Glu Glu Ala Lys Asp Arg Leu Arg Ile Leu Met Leu Arg Lys His
        210                 215                 220

Pro Arg Ser Leu Leu Ile Leu Asp Asp Val Trp Asp Ser Trp Val Leu
225                 230                 235                 240

Lys Ala Phe Asp Ser Gln Cys Gln Ile Leu Leu Thr Thr Arg Asp Lys
                245                 250                 255

Ser Val Thr Asp Ser Val Met Gly Pro Lys Tyr Val Pro Val Glu
            260                 265                 270

Ser Ser Leu Gly Lys Glu Lys Gly Leu Glu Ile Leu Ser Leu Phe Val
        275                 280                 285

Asn Met Lys Lys Ala Asp Leu Pro Glu Gln Ala His Ser Ile Ile Lys
    290                 295                 300

Glu Cys Lys Gly Ser Pro Leu Val Val Ser Leu Ile Gly Ala Leu Leu
305                 310                 315                 320

Arg Asp Phe Pro Asn Arg Trp Glu Tyr Tyr Leu Lys Gln Leu Gln Asn
                325                 330                 335

Lys Gln Phe Lys Arg Ile Arg Lys Ser Ser Tyr Asp Tyr Glu Ala
        340                 345                 350

Leu Asp Glu Ala Met Ser Ile Ser Val Glu Met Leu Arg Glu Asp Ile
    355                 360                 365

Lys Asp Tyr Tyr Thr Asp Leu Ser Ile Leu Gln Lys Asp Val Lys Val
        370                 375                 380

Pro Thr Lys Val Leu Cys Ile Leu Trp Asp Met Glu Thr Glu Glu Val
385                 390                 395                 400

Glu Asp Ile Leu Gln Glu Phe Val Asn Lys Ser Leu Leu Phe Cys Asp
                405                 410                 415

Arg Asn Gly Lys Ser Phe Arg Tyr Tyr Leu His Asp Leu Gln Val Asp
        420                 425                 430

Phe Leu Thr Glu Lys Asn Cys Ser Gln Leu Gln Asp Leu His Lys Lys
    435                 440                 445

Ile Ile Thr Gln Phe Gln Arg Tyr His Gln Pro His Thr Leu Ser Pro
        450                 455                 460

Asp Gln Glu Asp Cys Met Tyr Trp Tyr Asn Phe Leu Ala Tyr His Met
465                 470                 475                 480

Ala Ser Ala Lys Met His Lys Glu Leu Cys Ala Leu Met Phe Ser Leu
                485                 490                 495

Asp Trp Ile Lys Ala Lys Thr Glu Leu Val Gly Pro Ala His Leu Ile
        500                 505                 510

His Glu Phe Val Glu Tyr Arg His Ile Leu Asp Glu Lys Asp Cys Ala
    515                 520                 525

Val Ser Glu Asn Phe Gln Glu Phe Leu Ser Leu Asn Gly His Leu Leu
        530                 535                 540

Gly Arg Gln Pro Phe Pro Asn Ile Val Gln Leu Gly Leu Cys Glu Pro
545                 550                 555                 560

Glu Thr Ser Glu Val Tyr Gln Gln Ala Lys Leu Gln Ala Lys Gln Glu
```

```
                        565                 570                 575
Val Asp Asn Gly Met Leu Tyr Leu Glu Trp Ile Asn Lys Lys Asn Ile
                580                 585                 590
Thr Asn Leu Ser Arg Leu Val Val Arg Pro His Thr Asp Ala Val Tyr
            595                 600                 605
His Ala Cys Phe Ser Glu Asp Gly Gln Arg Ile Ala Ser Cys Gly Ala
        610                 615                 620
Asp Lys Thr Leu Gln Val Phe Lys Ala Glu Thr Gly Glu Lys Leu Leu
625                 630                 635                 640
Glu Ile Lys Ala His Glu Asp Glu Val Leu Cys Cys Ala Phe Ser Thr
                645                 650                 655
Asp Asp Arg Phe Ile Ala Thr Cys Ser Val Asp Lys Lys Val Lys Ile
            660                 665                 670
Trp Asn Ser Met Thr Gly Glu Leu Val His Thr Tyr Asp Glu His Ser
        675                 680                 685
Glu Gln Val Asn Cys Cys His Phe Thr Asn Ser Ser His His Leu Leu
    690                 695                 700
Leu Ala Thr Gly Ser Ser Asp Cys Phe Leu Lys Leu Trp Asp Leu Asn
705                 710                 715                 720
Gln Lys Glu Cys Arg Asn Thr Met Phe Gly His Thr Asn Ser Val Asn
                725                 730                 735
His Cys Arg Phe Ser Pro Asp Asp Lys Leu Leu Ala Ser Cys Ser Ala
            740                 745                 750
Asp Gly Thr Leu Lys Leu Trp Asp Ala Thr Ser Ala Asn Glu Arg Lys
        755                 760                 765
Ser Ile Asn Val Lys Gln Phe Phe Leu Asn Leu Glu Asp Pro Gln Glu
    770                 775                 780
Asp Met Glu Val Ile Val Lys Cys Cys Ser Trp Ser Ala Asp Gly Ala
785                 790                 795                 800
Arg Ile Met Val Ala Ala Lys Asn Lys Ile Phe Leu Trp Asn Thr Asp
                805                 810                 815
Ser Arg Ser Lys Val Ala Asp Cys Arg Gly His Leu Ser Trp Val His
            820                 825                 830
Gly Val Met Phe Ser Pro Asp Gly Ser Ser Phe Leu Thr Ser Ser Asp
        835                 840                 845
Asp Gln Thr Ile Arg Leu Trp Glu Thr Lys Lys Val Cys Lys Asn Ser
    850                 855                 860
Ala Val Met Leu Lys Gln Glu Val Asp Val Phe Gln Glu Asn Glu
865                 870                 875                 880
Val Met Val Leu Ala Val Asp His Ile Arg Arg Leu Gln Leu Ile Asn
                885                 890                 895
Gly Arg Thr Gly Gln Ile Asp Tyr Leu Thr Glu Ala Gln Val Ser Cys
            900                 905                 910
Cys Cys Leu Ser Pro His Leu Gln Tyr Ile Ala Phe Gly Asp Glu Asn
        915                 920                 925
Gly Ala Ile Glu Ile Leu Glu Leu Val Asn Asn Arg Ile Phe Gln Ser
    930                 935                 940
Arg Phe Gln His Lys Lys Thr Val Trp His Ile Gln Phe Thr Ala Asp
945                 950                 955                 960
Glu Lys Thr Leu Ile Ser Ser Ser Asp Asp Ala Glu Ile Gln Val Trp
                965                 970                 975
Asn Trp Gln Leu Asp Lys Cys Ile Phe Leu Arg Gly His Gln Glu Thr
            980                 985                 990
```

Val Lys Asp Phe Arg Leu Leu Lys Asn Ser Arg Leu Leu Ser Trp Ser
        995                 1000                1005

Phe Asp Gly Thr Val Lys Val Trp Asn Ile Ile Thr Gly Asn Lys
    1010                1015                1020

Glu Lys Asp Phe Val Cys His Gln Gly Thr Val Leu Ser Cys Asp
    1025                1030                1035

Ile Ser His Asp Ala Thr Lys Phe Ser Thr Ser Ala Asp Lys
    1040                1045                1050

Thr Ala Lys Ile Trp Ser Phe Asp Leu Leu Pro Leu His Glu
    1055                1060                1065

Leu Arg Gly His Asn Gly Cys Val Arg Cys Ser Ala Phe Ser Val
    1070                1075                1080

Asp Ser Thr Leu Leu Ala Thr Gly Asp Asp Asn Gly Glu Ile Arg
    1085                1090                1095

Ile Trp Asn Val Ser Asn Gly Glu Leu Leu His Leu Cys Ala Pro
    1100                1105                1110

Leu Ser Glu Glu Gly Ala Ala Thr His Gly Gly Trp Val Thr Asp
    1115                1120                1125

Leu Cys Phe Ser Pro Asp Gly Lys Met Leu Ile Ser Ala Gly Gly
    1130                1135                1140

Tyr Ile Lys Trp Trp Asn Val Val Thr Gly Glu Ser Ser Gln Thr
    1145                1150                1155

Phe Tyr Thr Asn Gly Thr Asn Leu Lys Lys Ile His Val Ser Pro
    1160                1165                1170

Asp Phe Lys Thr Tyr Val Thr Val Asp Asn Leu Gly Ile Leu Tyr
    1175                1180                1185

Ile Leu Gln Thr Leu Glu
    1190

<210> SEQ ID NO 3
<211> LENGTH: 1205
<212> TYPE: PRT
<213> ORGANISM: Homo sapiens

<400> SEQUENCE: 3

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
            20                  25                  30

Gly Phe Leu Thr Ile Ser Glu Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Val Phe Val Thr
        115                 120                 125

Arg Lys Lys Leu Val Asn Ala Ile Gln Gln Lys Leu Ser Lys Leu Lys
    130                 135                 140

Gly Glu Pro Gly Trp Val Thr Ile His Gly Met Ala Gly Cys Gly Lys

-continued

```
            145                 150                 155                 160
Ser Val Leu Ala Ala Glu Ala Val Arg Asp His Ser Leu Leu Glu Gly
                165                 170                 175
Cys Phe Pro Gly Gly Val His Trp Val Ser Val Gly Lys Gln Asp Lys
                180                 185                 190
Ser Gly Leu Leu Met Lys Leu Gln Asn Leu Cys Thr Arg Leu Asp Gln
                195                 200                 205
Asp Glu Ser Phe Ser Gln Arg Leu Pro Leu Asn Ile Glu Glu Ala Lys
                210                 215                 220
Asp Arg Leu Arg Ile Leu Met Leu Arg Lys His Pro Arg Ser Leu Leu
225                 230                 235                 240
Ile Leu Asp Asp Val Trp Asp Ser Trp Val Leu Lys Ala Phe Asp Ser
                245                 250                 255
Gln Cys Gln Ile Leu Leu Thr Thr Arg Asp Lys Ser Val Thr Asp Ser
                260                 265                 270
Val Met Gly Pro Lys Tyr Val Pro Val Glu Ser Ser Leu Gly Lys
                275                 280                 285
Glu Lys Gly Leu Glu Ile Leu Ser Leu Phe Val Asn Met Lys Lys Ala
                290                 295                 300
Asp Leu Pro Glu Gln Ala His Ser Ile Ile Lys Glu Cys Lys Gly Ser
305                 310                 315                 320
Pro Leu Val Val Ser Leu Ile Gly Ala Leu Leu Arg Asp Phe Pro Asn
                325                 330                 335
Arg Trp Glu Tyr Tyr Leu Lys Gln Leu Gln Asn Lys Gln Phe Lys Arg
                340                 345                 350
Ile Arg Lys Ser Ser Ser Tyr Asp Tyr Glu Ala Leu Asp Glu Ala Met
                355                 360                 365
Ser Ile Ser Val Glu Met Leu Arg Glu Asp Ile Lys Asp Tyr Tyr Thr
                370                 375                 380
Asp Leu Ser Ile Leu Gln Lys Asp Val Lys Val Pro Thr Lys Val Leu
385                 390                 395                 400
Cys Ile Leu Trp Asp Met Glu Thr Glu Glu Val Glu Asp Ile Leu Gln
                405                 410                 415
Glu Phe Val Asn Lys Ser Leu Leu Phe Cys Asp Arg Asn Gly Lys Ser
                420                 425                 430
Phe Arg Tyr Tyr Leu His Asp Leu Gln Val Asp Phe Leu Thr Glu Lys
                435                 440                 445
Asn Cys Ser Gln Leu Gln Asp Leu His Lys Lys Ile Ile Thr Gln Phe
                450                 455                 460
Gln Arg Tyr His Gln Pro His Thr Leu Ser Pro Asp Gln Glu Asp Cys
465                 470                 475                 480
Met Tyr Trp Tyr Asn Phe Leu Ala Tyr His Met Ala Ser Ala Lys Met
                485                 490                 495
His Lys Glu Leu Cys Ala Leu Met Phe Ser Leu Asp Trp Ile Lys Ala
                500                 505                 510
Lys Thr Glu Leu Val Gly Pro Ala His Leu Ile His Glu Phe Val Glu
                515                 520                 525
Tyr Arg His Ile Leu Asp Glu Lys Asp Cys Ala Val Ser Glu Asn Phe
                530                 535                 540
Gln Glu Phe Leu Ser Leu Asn Gly His Leu Leu Gly Arg Gln Pro Phe
545                 550                 555                 560
Pro Asn Ile Val Gln Leu Gly Leu Cys Glu Pro Glu Thr Ser Glu Val
                565                 570                 575
```

```
Tyr Gln Gln Ala Lys Leu Gln Ala Lys Gln Glu Val Asp Asn Gly Met
            580                 585                 590

Leu Tyr Leu Glu Trp Ile Asn Lys Lys Asn Ile Thr Asn Leu Ser Arg
            595                 600                 605

Leu Val Val Arg Pro His Thr Asp Ala Val Tyr His Ala Cys Phe Ser
            610                 615                 620

Glu Asp Gly Gln Arg Ile Ala Ser Cys Gly Ala Asp Lys Thr Leu Gln
625                 630                 635                 640

Val Phe Lys Ala Glu Thr Gly Glu Lys Leu Leu Glu Ile Lys Ala His
            645                 650                 655

Glu Asp Glu Val Leu Cys Cys Ala Phe Ser Thr Asp Asp Arg Phe Ile
            660                 665                 670

Ala Thr Cys Ser Val Asp Lys Lys Val Lys Ile Trp Asn Ser Met Thr
            675                 680                 685

Gly Glu Leu Val His Thr Tyr Asp Glu His Ser Glu Gln Val Asn Cys
            690                 695                 700

Cys His Phe Ala Asn Ser Ser His Leu Leu Leu Ala Thr Gly Ser
705                 710                 715                 720

Ser Asp Cys Phe Leu Lys Leu Trp Asp Leu Asn Gln Lys Glu Cys Arg
            725                 730                 735

Asn Thr Met Phe Gly His Thr Asn Ser Val Asn His Cys Arg Phe Ser
            740                 745                 750

Pro Asp Asp Lys Leu Leu Ala Ser Cys Ser Ala Asp Gly Thr Leu Lys
            755                 760                 765

Leu Trp Asp Ala Thr Ser Ala Asn Glu Arg Lys Ser Ile Asn Val Lys
770                 775                 780

Gln Phe Phe Leu Asn Leu Glu Asp Pro Gln Glu Asp Met Glu Val Ile
785                 790                 795                 800

Val Lys Cys Cys Ser Trp Ser Ala Asp Gly Ala Arg Ile Met Val Ala
            805                 810                 815

Ala Lys Asn Lys Ile Phe Leu Trp Asn Thr Asp Ser Arg Ser Lys Val
            820                 825                 830

Ala Asp Cys Arg Gly His Leu Ser Trp Val His Gly Val Met Phe Ser
            835                 840                 845

Pro Asp Gly Ser Ser Phe Leu Thr Ser Ser Asp Gln Thr Ile Arg
            850                 855                 860

Leu Trp Glu Thr Lys Lys Val Cys Lys Asn Ser Ala Val Met Leu Lys
865                 870                 875                 880

Gln Glu Val Asp Val Val Phe Gln Glu Asn Glu Val Met Val Leu Ala
            885                 890                 895

Val Asp His Ile Arg Arg Leu Gln Leu Ile Asn Gly Arg Thr Gly Gln
            900                 905                 910

Ile Asp Tyr Leu Thr Glu Ala Gln Val Ser Cys Cys Cys Leu Ser Pro
            915                 920                 925

His Leu Gln Tyr Ile Ala Phe Gly Asp Glu Asn Gly Ala Ile Glu Ile
            930                 935                 940

Leu Glu Leu Val Asn Asn Arg Ile Phe Gln Ser Arg Phe Gln His Lys
945                 950                 955                 960

Lys Thr Val Trp His Ile Gln Phe Thr Ala Asp Glu Lys Thr Leu Ile
            965                 970                 975

Ser Ser Ser Asp Asp Ala Glu Ile Gln Val Trp Asn Trp Gln Leu Asp
            980                 985                 990
```

```
Lys Cys Ile Phe Leu Arg Gly His  Gln Glu Thr Val Lys  Asp Phe Arg
        995              1000                1005

Leu Leu Lys Asn Ser Arg Leu  Leu Ser Trp Ser Phe  Asp Gly Thr
        1010             1015              1020

Val Lys Val Trp Asn Ile Ile  Thr Gly Asn Lys Glu  Lys Asp Phe
        1025             1030              1035

Val Cys His Gln Gly Thr Val  Leu Ser Cys Asp Ile  Ser His Asp
        1040             1045              1050

Ala Thr Lys Phe Ser Ser Thr  Ser Ala Asp Lys Thr  Ala Lys Ile
        1055             1060              1065

Trp Ser Phe Asp Leu Leu Leu  Pro Leu His Glu Leu  Arg Gly His
        1070             1075              1080

Asn Gly Cys Val Arg Cys Ser  Ala Phe Ser Val Asp  Ser Thr Leu
        1085             1090              1095

Leu Ala Thr Gly Asp Asp Asn  Gly Glu Ile Arg Ile  Trp Asn Val
        1100             1105              1110

Ser Asn Gly Glu Leu Leu His  Leu Cys Ala Pro Leu  Ser Glu Glu
        1115             1120              1125

Gly Ala Ala Thr His Gly Gly  Trp Val Thr Asp Leu  Cys Phe Ser
        1130             1135              1140

Pro Asp Gly Lys Met Leu Ile  Ser Ala Gly Gly Tyr  Ile Lys Trp
        1145             1150              1155

Trp Asn Val Val Thr Gly Glu  Ser Ser Gln Thr Phe  Tyr Thr Asn
        1160             1165              1170

Gly Thr Asn Leu Lys Lys Ile  His Val Ser Pro Asp  Phe Lys Thr
        1175             1180              1185

Tyr Val Thr Val Asp Asn Leu  Gly Ile Leu Tyr Ile  Leu Gln Thr
        1190             1195              1200

Leu Glu
    1205

<210> SEQ ID NO 4
<211> LENGTH: 1237
<212> TYPE: PRT
<213> ORGANISM: Homo sapiens

<400> SEQUENCE: 4

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu His Glu Gly Tyr
65                  70                  75                  80

Lys Asp Leu Ala Ala Leu Leu His Asp Gly Ile Pro Val Val Ser Ser
                85                  90                  95

Ser Ser Val Arg Thr Val Leu Cys Glu Gly Gly Val Pro Gln Arg Pro
            100                 105                 110

Val Val Phe Val Thr Arg Lys Lys Leu Val Asn Ala Ile Gln Gln Lys
        115                 120                 125

Leu Ser Lys Leu Lys Gly Glu Pro Gly Trp Val Thr Ile His Gly Met
    130                 135                 140
```

-continued

```
Ala Gly Cys Gly Lys Ser Val Leu Ala Ala Glu Ala Val Arg Asp His
145                 150                 155                 160

Ser Leu Leu Glu Gly Cys Phe Pro Gly Gly Val His Trp Val Ser Val
                165                 170                 175

Gly Lys Gln Asp Lys Ser Gly Leu Leu Met Lys Leu Gln Asn Leu Cys
            180                 185                 190

Thr Arg Leu Asp Gln Asp Glu Ser Phe Ser Gln Arg Leu Pro Leu Asn
        195                 200                 205

Ile Glu Glu Ala Lys Asp Arg Leu Arg Ile Leu Met Leu Arg Lys His
    210                 215                 220

Pro Arg Ser Leu Leu Ile Leu Asp Asp Val Trp Asp Ser Trp Val Leu
225                 230                 235                 240

Lys Ala Phe Asp Ser Gln Cys Gln Ile Leu Thr Thr Arg Asp Lys
                245                 250                 255

Ser Val Thr Asp Ser Val Met Gly Pro Lys Tyr Val Pro Val Glu
                260                 265                 270

Ser Ser Leu Gly Lys Glu Lys Gly Leu Glu Ile Leu Ser Leu Phe Val
                275                 280                 285

Asn Met Lys Lys Ala Asp Leu Pro Glu Gln Ala His Ser Ile Ile Lys
        290                 295                 300

Glu Cys Lys Gly Ser Pro Leu Val Val Ser Leu Ile Gly Ala Leu Leu
305                 310                 315                 320

Arg Asp Phe Pro Asn Arg Trp Glu Tyr Tyr Leu Lys Gln Leu Gln Asn
                325                 330                 335

Lys Gln Phe Lys Arg Ile Arg Lys Ser Ser Tyr Asp Tyr Glu Ala
            340                 345                 350

Leu Asp Glu Ala Met Ser Ile Ser Val Glu Met Leu Arg Glu Asp Ile
        355                 360                 365

Lys Asp Tyr Tyr Thr Asp Leu Ser Ile Leu Gln Lys Asp Val Lys Val
    370                 375                 380

Pro Thr Lys Val Leu Cys Ile Leu Trp Asp Met Glu Thr Glu Glu Val
385                 390                 395                 400

Glu Asp Ile Leu Gln Glu Phe Val Asn Lys Ser Leu Leu Phe Cys Asp
                405                 410                 415

Arg Asn Gly Lys Ser Phe Arg Tyr Tyr Leu His Asp Leu Gln Val Asp
            420                 425                 430

Phe Leu Thr Glu Lys Asn Cys Ser Gln Leu Gln Asp Leu His Lys Lys
        435                 440                 445

Ile Ile Thr Gln Phe Gln Arg Tyr His Gln Pro His Thr Leu Ser Pro
    450                 455                 460

Asp Gln Glu Asp Cys Met Tyr Trp Tyr Asn Phe Leu Ala Tyr His Met
465                 470                 475                 480

Ala Ser Ala Lys Met His Lys Glu Leu Cys Ala Leu Met Phe Ser Leu
                485                 490                 495

Asp Trp Ile Lys Ala Lys Thr Glu Leu Val Gly Pro Ala His Leu Ile
            500                 505                 510

His Glu Phe Val Glu Tyr Arg His Ile Leu Asp Glu Lys Asp Cys Ala
        515                 520                 525

Val Ser Glu Asn Phe Gln Glu Phe Leu Ser Leu Asn Gly His Leu Leu
    530                 535                 540

Gly Arg Gln Pro Phe Pro Asn Ile Val Gln Leu Gly Leu Cys Glu Pro
545                 550                 555                 560
```

-continued

```
Glu Thr Ser Glu Val Tyr Gln Gln Ala Lys Leu Gln Ala Lys Gln Glu
                565                 570                 575

Val Asp Asn Gly Met Leu Tyr Leu Glu Trp Ile Asn Lys Lys Asn Ile
            580                 585                 590

Thr Asn Leu Ser Arg Leu Val Val Arg Pro His Thr Asp Ala Val Tyr
        595                 600                 605

His Ala Cys Phe Ser Glu Asp Gly Gln Arg Ile Ala Ser Cys Gly Ala
    610                 615                 620

Asp Lys Thr Leu Gln Val Phe Lys Ala Glu Thr Gly Glu Lys Leu Leu
625                 630                 635                 640

Glu Ile Lys Ala His Glu Asp Glu Val Leu Cys Cys Ala Phe Ser Thr
                645                 650                 655

Asp Asp Arg Phe Ile Ala Thr Cys Ser Val Asp Lys Lys Val Lys Ile
            660                 665                 670

Trp Asn Ser Met Thr Gly Glu Leu Val His Thr Tyr Asp Glu His Ser
        675                 680                 685

Glu Gln Val Asn Cys Cys His Phe Thr Asn Ser Ser His His Leu Leu
    690                 695                 700

Leu Ala Thr Gly Ser Ser Asp Cys Phe Leu Lys Leu Trp Asp Leu Asn
705                 710                 715                 720

Gln Lys Glu Cys Arg Asn Thr Met Phe Gly His Thr Asn Ser Val Asn
                725                 730                 735

His Cys Arg Phe Ser Pro Asp Asp Lys Leu Leu Ala Ser Cys Ser Ala
            740                 745                 750

Asp Gly Thr Leu Lys Leu Trp Asp Ala Thr Ser Ala Asn Glu Arg Lys
        755                 760                 765

Ser Ile Asn Val Lys Gln Phe Phe Leu Asn Leu Glu Asp Pro Gln Glu
    770                 775                 780

Asp Met Glu Val Ile Val Lys Cys Cys Ser Trp Ser Ala Asp Gly Ala
785                 790                 795                 800

Arg Ile Met Val Ala Ala Lys Asn Lys Ile Phe Leu Phe Asp Ile His
                805                 810                 815

Thr Ser Gly Leu Leu Gly Glu Ile His Thr Gly His His Ser Thr Ile
            820                 825                 830

Gln Tyr Cys Asp Phe Ser Pro Gln Asn His Leu Ala Val Val Ala Leu
        835                 840                 845

Ser Gln Tyr Cys Val Glu Leu Trp Asn Thr Asp Ser Arg Ser Lys Val
    850                 855                 860

Ala Asp Cys Arg Gly His Leu Ser Trp Val His Gly Val Met Phe Ser
865                 870                 875                 880

Pro Asp Gly Ser Ser Phe Leu Thr Ser Ser Asp Asp Gln Thr Ile Arg
                885                 890                 895

Leu Trp Glu Thr Lys Lys Val Cys Lys Asn Ser Ala Val Met Leu Lys
            900                 905                 910

Gln Glu Val Asp Val Val Phe Gln Glu Asn Glu Val Met Val Leu Ala
        915                 920                 925

Val Asp His Ile Arg Arg Leu Gln Leu Ile Asn Gly Arg Thr Gly Gln
    930                 935                 940

Ile Asp Tyr Leu Thr Glu Ala Gln Val Ser Cys Cys Cys Leu Ser Pro
945                 950                 955                 960

His Leu Gln Tyr Ile Ala Phe Gly Asp Glu Asn Gly Ala Ile Glu Ile
                965                 970                 975

Leu Glu Leu Val Asn Asn Arg Ile Phe Gln Ser Arg Phe Gln His Lys
```

-continued

```
                    980                985                990
Lys Thr Val Trp His Ile Gln Phe  Thr Ala Asp Glu Lys  Thr Leu Ile
                995               1000               1005

Ser Ser  Ser Asp Asp Ala Glu  Ile Gln Val Trp Asn  Trp Gln Leu
         1010              1015              1020

Asp Lys  Cys Ile Phe Leu Arg  Gly His Gln Glu Thr  Val Lys Asp
         1025              1030              1035

Phe Arg  Leu Leu Lys Asn Ser  Arg Leu Ser Trp  Ser Phe Asp
         1040              1045              1050

Gly Thr  Val Lys Val Trp Asn  Ile Ile Thr Gly Asn  Lys Glu Lys
         1055              1060              1065

Asp Phe  Val Cys His Gln Gly  Thr Val Leu Ser Cys  Asp Ile Ser
         1070              1075              1080

His Asp  Ala Thr Lys Phe Ser  Ser Thr Ser Ala Asp  Lys Thr Ala
         1085              1090              1095

Lys Ile  Trp Ser Phe Asp Leu  Leu Leu Pro Leu His  Glu Leu Arg
         1100              1105              1110

Gly His  Asn Gly Cys Val Arg  Cys Ser Ala Phe Ser  Val Asp Ser
         1115              1120              1125

Thr Leu  Leu Ala Thr Gly Asp  Asp Asn Gly Glu Ile  Arg Ile Trp
         1130              1135              1140

Asn Val  Ser Asn Gly Glu Leu  Leu His Leu Cys Ala  Pro Leu Ser
         1145              1150              1155

Glu Glu  Gly Ala Ala Thr His  Gly Gly Trp Val Thr  Asp Leu Cys
         1160              1165              1170

Phe Ser  Pro Asp Gly Lys Met  Leu Ile Ser Ala Gly  Gly Tyr Ile
         1175              1180              1185

Lys Trp  Trp Asn Val Val Thr  Gly Glu Ser Ser Gln  Thr Phe Tyr
         1190              1195              1200

Thr Asn  Gly Thr Asn Leu Lys  Lys Ile His Val Ser  Pro Asp Phe
         1205              1210              1215

Lys Thr  Tyr Val Thr Val Asp  Asn Leu Gly Ile Leu  Tyr Ile Leu
         1220              1225              1230

Gln Thr  Leu Glu
         1235

<210> SEQ ID NO 5
<211> LENGTH: 1248
<212> TYPE: PRT
<213> ORGANISM: Homo sapiens

<400> SEQUENCE: 5

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
                20                  25                  30

Gly Phe Leu Thr Ile Ser Glu Glu Lys Val Arg Asn Glu Pro Thr
            35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu His Glu Gly Tyr
65                  70                  75                  80

Lys Asp Leu Ala Ala Leu Leu His Asp Gly Ile Pro Val Val Ser Ser
                85                  90                  95
```

```
Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Phe Val Thr
        115                 120                 125

Arg Lys Lys Leu Val Asn Ala Ile Gln Gln Lys Leu Ser Lys Leu Lys
        130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
                165                 170                 175

Cys Phe Pro Gly Gly Val His Trp Val Ser Val Gly Lys Gln Asp Lys
                180                 185                 190

Ser Gly Leu Leu Met Lys Leu Gln Asn Leu Cys Thr Arg Leu Asp Gln
            195                 200                 205

Asp Glu Ser Phe Ser Gln Arg Leu Pro Leu Asn Ile Glu Glu Ala Lys
        210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
                245                 250                 255

Gln Cys Gln Ile Leu Leu Thr Thr Arg Asp Lys Ser Val Thr Asp Ser
            260                 265                 270

Val Met Gly Pro Lys Tyr Val Pro Val Glu Ser Ser Leu Gly Lys
        275                 280                 285

Glu Lys Gly Leu Glu Ile Leu Ser Leu Phe Val Asn Met Lys Lys Ala
        290                 295                 300

Asp Leu Pro Glu Gln Ala His Ser Ile Ile Lys Glu Cys Lys Gly Ser
305                 310                 315                 320

Pro Leu Val Val Ser Leu Ile Gly Ala Leu Leu Arg Asp Phe Pro Asn
                325                 330                 335

Arg Trp Glu Tyr Tyr Leu Lys Gln Leu Gln Asn Lys Gln Phe Lys Arg
                340                 345                 350

Ile Arg Lys Ser Ser Ser Tyr Asp Tyr Glu Ala Leu Asp Glu Ala Met
            355                 360                 365

Ser Ile Ser Val Glu Met Leu Arg Glu Asp Ile Lys Asp Tyr Tyr Thr
        370                 375                 380

Asp Leu Ser Ile Leu Gln Lys Asp Val Lys Val Pro Thr Lys Val Leu
385                 390                 395                 400

Cys Ile Leu Trp Asp Met Glu Thr Glu Glu Val Glu Asp Ile Leu Gln
                405                 410                 415

Glu Phe Val Asn Lys Ser Leu Leu Phe Cys Asp Arg Asn Gly Lys Ser
                420                 425                 430

Phe Arg Tyr Tyr Leu His Asp Leu Gln Val Asp Phe Leu Thr Glu Lys
            435                 440                 445

Asn Cys Ser Gln Leu Gln Asp Leu His Lys Lys Ile Thr Gln Phe
        450                 455                 460

Gln Arg Tyr His Gln Pro His Thr Leu Ser Pro Asp Gln Glu Asp Cys
465                 470                 475                 480

Met Tyr Trp Tyr Asn Phe Leu Ala Tyr His Met Ala Ser Ala Lys Met
                485                 490                 495

His Lys Glu Leu Cys Ala Leu Met Phe Ser Leu Asp Trp Ile Lys Ala
            500                 505                 510

Lys Thr Glu Leu Val Gly Pro Ala His Leu Ile His Glu Phe Val Glu
```

-continued

```
                515                 520                 525
Tyr Arg His Ile Leu Asp Glu Lys Asp Cys Ala Val Ser Glu Asn Phe
            530                 535                 540
Gln Glu Phe Leu Ser Leu Asn Gly His Leu Leu Gly Arg Gln Pro Phe
545                 550                 555                 560
Pro Asn Ile Val Gln Leu Gly Leu Cys Glu Pro Glu Thr Ser Glu Val
                565                 570                 575
Tyr Gln Gln Ala Lys Leu Gln Ala Lys Gln Glu Val Asp Asn Gly Met
            580                 585                 590
Leu Tyr Leu Glu Trp Ile Asn Lys Lys Asn Ile Thr Asn Leu Ser Arg
            595                 600                 605
Leu Val Val Arg Pro His Thr Asp Ala Val Tyr His Ala Cys Phe Ser
        610                 615                 620
Glu Asp Gly Gln Arg Ile Ala Ser Cys Gly Ala Asp Lys Thr Leu Gln
625                 630                 635                 640
Val Phe Lys Ala Glu Thr Gly Glu Lys Leu Leu Glu Ile Lys Ala His
                645                 650                 655
Glu Asp Glu Val Leu Cys Cys Ala Phe Ser Thr Asp Arg Phe Ile
            660                 665                 670
Ala Thr Cys Ser Val Asp Lys Lys Val Lys Ile Trp Asn Ser Met Thr
        675                 680                 685
Gly Glu Leu Val His Thr Tyr Asp Glu His Ser Glu Gln Val Asn Cys
        690                 695                 700
Cys His Phe Thr Asn Ser Ser His His Leu Leu Leu Ala Thr Gly Ser
705                 710                 715                 720
Ser Asp Cys Phe Leu Lys Leu Trp Asp Leu Asn Gln Lys Glu Cys Arg
                725                 730                 735
Asn Thr Met Phe Gly His Thr Asn Ser Val Asn His Cys Arg Phe Ser
            740                 745                 750
Pro Asp Lys Leu Leu Ala Ser Cys Ser Ala Asp Gly Thr Leu Lys
            755                 760                 765
Leu Trp Asp Ala Thr Ser Ala Asn Glu Arg Lys Ser Ile Asn Val Lys
        770                 775                 780
Gln Phe Phe Leu Asn Leu Glu Asp Pro Gln Glu Asp Met Glu Val Ile
785                 790                 795                 800
Val Lys Cys Cys Ser Trp Ser Ala Asp Gly Ala Arg Ile Met Val Ala
                805                 810                 815
Ala Lys Asn Lys Ile Phe Leu Phe Asp Ile His Thr Ser Gly Leu Leu
            820                 825                 830
Gly Glu Ile His Thr Gly His His Ser Thr Ile Gln Tyr Cys Asp Phe
            835                 840                 845
Ser Pro Gln Asn His Leu Ala Val Val Ala Leu Ser Gln Tyr Cys Val
        850                 855                 860
Glu Leu Trp Asn Thr Asp Ser Arg Ser Lys Val Ala Asp Cys Arg Gly
865                 870                 875                 880
His Leu Ser Trp Val His Gly Val Met Phe Ser Pro Asp Gly Ser Ser
                885                 890                 895
Phe Leu Thr Ser Ser Asp Asp Gln Thr Ile Arg Leu Trp Glu Thr Lys
            900                 905                 910
Lys Val Cys Lys Asn Ser Ala Val Met Leu Lys Gln Glu Val Asp Val
            915                 920                 925
Val Phe Gln Glu Asn Glu Val Met Val Leu Ala Val Asp His Ile Arg
        930                 935                 940
```

```
Arg Leu Gln Leu Ile Asn Gly Arg Thr Gly Gln Ile Asp Tyr Leu Thr
945                 950                 955                 960

Glu Ala Gln Val Ser Cys Cys Cys Leu Ser Pro His Leu Gln Tyr Ile
                965                 970                 975

Ala Phe Gly Asp Glu Asn Gly Ala Ile Glu Ile Leu Glu Leu Val Asn
            980                 985                 990

Asn Arg Ile Phe Gln Ser Arg Phe Gln His Lys Lys Thr Val Trp His
        995                 1000                1005

Ile Gln Phe Thr Ala Asp Glu Lys Thr Leu Ile Ser Ser Ser Asp
    1010                1015                1020

Asp Ala Glu Ile Gln Val Trp Asn Trp Gln Leu Asp Lys Cys Ile
    1025                1030                1035

Phe Leu Arg Gly His Gln Glu Thr Val Lys Asp Phe Arg Leu Leu
    1040                1045                1050

Lys Asn Ser Arg Leu Leu Ser Trp Ser Phe Asp Gly Thr Val Lys
    1055                1060                1065

Val Trp Asn Ile Ile Thr Gly Asn Lys Glu Lys Asp Phe Val Cys
    1070                1075                1080

His Gln Gly Thr Val Leu Ser Cys Asp Ile Ser His Asp Ala Thr
    1085                1090                1095

Lys Phe Ser Ser Thr Ser Ala Asp Lys Thr Ala Lys Ile Trp Ser
    1100                1105                1110

Phe Asp Leu Leu Leu Pro Leu His Glu Leu Arg Gly His Asn Gly
    1115                1120                1125

Cys Val Arg Cys Ser Ala Phe Ser Val Asp Ser Thr Leu Leu Ala
    1130                1135                1140

Thr Gly Asp Asp Asn Gly Glu Ile Arg Ile Trp Asn Val Ser Asn
    1145                1150                1155

Gly Glu Leu Leu His Leu Cys Ala Pro Leu Ser Glu Glu Gly Ala
    1160                1165                1170

Ala Thr His Gly Gly Trp Val Thr Asp Leu Cys Phe Ser Pro Asp
    1175                1180                1185

Gly Lys Met Leu Ile Ser Ala Gly Gly Tyr Ile Lys Trp Trp Asn
    1190                1195                1200

Val Val Thr Gly Glu Ser Ser Gln Thr Phe Tyr Thr Asn Gly Thr
    1205                1210                1215

Asn Leu Lys Lys Ile His Val Ser Pro Asp Phe Lys Thr Tyr Val
    1220                1225                1230

Thr Val Asp Asn Leu Gly Ile Leu Tyr Ile Leu Gln Thr Leu Glu
    1235                1240                1245

<210> SEQ ID NO 6
<211> LENGTH: 600
<212> TYPE: PRT
<213> ORGANISM: Danio rerio

<400> SEQUENCE: 6

Met Glu Glu Arg Ala Arg Ser Arg Leu Leu Arg Ser Lys Ala Thr Leu
1               5                   10                  15

Glu Gln Asp Ile Lys Ala Ser Tyr Leu Met Asp His Met Ile Ser Asp
                20                  25                  30

Gly Val Leu Thr Asn Asp Glu Glu Ala Lys Val Leu Ser Lys Ala Thr
            35                  40                  45

Arg Lys Glu Gln Ala Val Ala Leu Leu Glu Thr Leu Leu Arg Lys Asp
```

-continued

```
                    50                  55                  60
Asn Arg Ala Tyr Ile Ser Phe Tyr Asn Ala Leu Ile Arg Glu Ser Tyr
 65                  70                  75                  80

Gly Asp Leu Ala Ser Leu Leu His Ser Asp Leu Pro Leu Leu Ser Pro
                     85                  90                  95

Glu Gly Glu Lys Ser Phe Ala Asp Gly Val Ser Pro Val Gln Ala
                    100                 105                 110

Ile Leu Ser Val Gly Gly Val Pro Gln Arg Pro Val Phe Val Ser
                115                 120                 125

Arg Pro Pro Leu Leu Asn Leu Ile Arg Glu Met Leu Tyr Gln Leu Arg
130                 135                 140

Asp Thr Pro Gly Trp Val Thr Val Phe Gly Met Ala Gly Ser Gly Lys
145                 150                 155                 160

Ser Val Met Ala Ala Glu Val Val Arg Asp Arg Ser Leu Ile Lys Glu
                165                 170                 175

Cys Phe Pro Asp Gly Val His Trp Leu Ser Val Gly Gln Cys Glu Arg
                180                 185                 190

Ala Asp Leu Leu Val Arg Met Gln Ser Leu Cys Phe Arg Leu Glu Gln
                195                 200                 205

Cys Gln Ser Ser Asp Thr Ser Gln Arg Pro Pro Ser Thr Val Glu Glu
                210                 215                 220

Ala Lys Glu Arg Leu Arg Phe Leu Met Leu Arg Arg Phe Pro Arg Ser
225                 230                 235                 240

Leu Leu Ile Leu Asp Asp Val Trp Asp Ser Ser Leu Arg Ser Phe
                    245                 250                 255

Asp Ile Gln Cys Arg Val Leu Leu Thr Thr Arg Asn Arg Ala Leu Thr
                260                 265                 270

Asp Ser Val Ser Gly Val Arg Tyr Glu Val Pro Val Glu Asn Gly Leu
                275                 280                 285

Asp Glu Glu Lys Ala Leu Glu Ile Leu Ala Leu Tyr Val Asn Gly Lys
                290                 295                 300

Met His Lys Leu Pro Glu Gln Ala Arg Ser Ile Val Ser Glu Cys Lys
305                 310                 315                 320

Gly Ser Pro Leu Val Val Ser Leu Ile Gly Ala Leu Leu Arg Glu Phe
                    325                 330                 335

Pro Asp Arg Trp Ser Tyr Tyr Leu Arg Gln Leu Gln Gln Lys Gln Phe
                    340                 345                 350

Lys Arg Ile Arg Lys Ser Ser Tyr Asp Tyr Glu Ala Leu Asp Gln
                355                 360                 365

Ala Met Asp Ala Ser Leu Gln Val Leu Glu Ala Glu His Gln Glu Leu
370                 375                 380

Tyr Arg Asp Leu Ser Val Met Gln Lys Asp Ile Lys Val Pro Ala Lys
385                 390                 395                 400

Val Leu Ser Val Leu Trp Gly Leu Glu Leu Glu Val Glu Asp Val
                    405                 410                 415

Leu Gln Glu Phe Val Asn Lys Ser Leu Leu Phe Arg Asp Cys Asn Gln
                420                 425                 430

Arg Pro Tyr Arg Tyr Leu His Asp Leu Gln Leu Asp Phe Leu Ala
                435                 440                 445

Glu Gln Asn Arg Asp Gln Ile Ala Glu Leu His Lys Lys Met Val Arg
                450                 455                 460

Gln Tyr Gln Arg Phe Tyr Ser Lys Arg Pro Pro Asp Ser Ala Asp Lys
465                 470                 475                 480
```

```
Asp Ser Leu Tyr Trp Tyr Gln Phe Ile Pro Tyr His Met Ala Lys Ala
            485                 490                 495

Gly Leu Ser Lys Glu Leu Tyr Ser Leu Met Phe Ser Leu Asp Trp Val
            500                 505                 510

Lys Glu Lys Ala Arg Ile Met Gly Ser Ala His Leu Ile Asn Asp Tyr
            515                 520                 525

Val Glu Tyr Gly Glu Ile Leu Asp Lys Glu Asn Ser Glu Val Arg Val
            530                 535                 540

Gln Phe Gln Glu Phe Leu Ser Leu Asn Gly His His Leu Glu Gln Arg
545                 550                 555                 560

Pro Phe Pro Asp Val Val Gln Leu Ala Leu Ser Gln Pro Asp Arg Ser
            565                 570                 575

Glu Val Tyr Arg Gln Ala Leu Met Gln Ala Gln Lys Arg Ala Ser Arg
            580                 585                 590

Gly Gln Ile Tyr Leu Asn Trp Val
            595                 600

<210> SEQ ID NO 7
<211> LENGTH: 588
<212> TYPE: PRT
<213> ORGANISM: Drosophila melanogaster

<400> SEQUENCE: 7

Met Asp Phe Glu Thr Gly Glu His Gln Tyr Gln Tyr Lys Asp Ile Leu
1               5                   10                  15

Ser Val Phe Glu Asp Ala Phe Val Asp Asn Phe Asp Cys Lys Asp Val
                20                  25                  30

Gln Asp Met Pro Lys Ser Ile Leu Ser Lys Glu Glu Ile Asp His Ile
            35                  40                  45

Ile Met Ser Lys Asp Ala Val Ser Gly Thr Leu Arg Leu Phe Trp Thr
        50                  55                  60

Leu Leu Ser Lys Gln Glu Met Val Gln Lys Phe Val Glu Glu Val
65                  70                  75                  80

Leu Arg Ile Asn Tyr Lys Phe Leu Met Ser Pro Ile Lys Thr Glu Gln
                85                  90                  95

Arg Gln Pro Ser Met Met Thr Arg Met Tyr Ile Glu Gln Arg Asp Arg
            100                 105                 110

Leu Tyr Asn Asp Asn Gln Val Phe Ala Lys Tyr Asn Val Ser Arg Leu
        115                 120                 125

Gln Pro Tyr Leu Lys Leu Arg Gln Ala Leu Leu Glu Leu Arg Pro Ala
    130                 135                 140

Lys Asn Val Leu Ile Asp Gly Leu Gly Ser Gly Lys Thr Trp Val
145                 150                 155                 160

Ala Leu Asp Val Cys Leu Ser Tyr Lys Val Gln Cys Lys Met Asp Phe
                165                 170                 175

Lys Ile Phe Trp Leu Asn Leu Lys Asn Cys Asn Ser Pro Glu Thr Val
            180                 185                 190

Leu Glu Met Leu Gln Lys Leu Tyr Gln Ile Asp Pro Asn Trp Thr
        195                 200                 205

Ser Arg Ser Asp His Ser Ser Asn Ile Lys Leu Arg Ile His Ser Ile
    210                 215                 220

Gln Ala Glu Leu Arg Arg Leu Lys Ser Lys Pro Tyr Glu Asn Cys
225                 230                 235                 240

Leu Leu Val Leu Leu Asn Val Gln Asn Ala Lys Ala Trp Asn Ala Phe
```

```
                    245                 250                 255
Asn Leu Ser Cys Lys Ile Leu Leu Thr Thr Arg Phe Lys Gln Val Thr
            260                 265                 270

Asp Phe Leu Ser Ala Ala Thr Thr His Ile Ser Leu Asp His His
        275                 280                 285

Ser Met Thr Leu Thr Pro Asp Glu Val Lys Ser Leu Leu Lys Tyr
    290                 295                 300

Leu Asp Cys Arg Pro Gln Asp Leu Pro Arg Glu Val Leu Thr Thr Asn
305                 310                 315                 320

Pro Arg Arg Leu Ser Ile Ile Ala Glu Ser Ile Arg Asp Gly Leu Ala
                325                 330                 335

Thr Trp Asp Asn Trp Lys His Val Asn Cys Asp Lys Leu Thr Thr Ile
            340                 345                 350

Ile Glu Ser Ser Leu Asn Val Leu Glu Pro Ala Glu Tyr Arg Lys Met
        355                 360                 365

Phe Asp Arg Leu Ser Val Phe Pro Pro Ser Ala His Ile Pro Thr Ile
    370                 375                 380

Leu Leu Ser Leu Ile Trp Phe Asp Val Ile Lys Ser Asp Val Met Val
385                 390                 395                 400

Val Val Asn Lys Leu His Lys Tyr Ser Leu Val Glu Lys Gln Pro Lys
                405                 410                 415

Glu Ser Thr Ile Ser Ile Pro Ser Ile Tyr Leu Glu Leu Lys Val Lys
            420                 425                 430

Leu Glu Asn Glu Tyr Ala Leu His Arg Ser Ile Val Asp His Tyr Asn
        435                 440                 445

Ile Pro Lys Thr Phe Asp Ser Asp Leu Ile Pro Pro Tyr Leu Asp
    450                 455                 460

Gln Tyr Phe Tyr Ser His Ile Gly His His Leu Lys Asn Ile Glu His
465                 470                 475                 480

Pro Glu Arg Met Thr Leu Phe Arg Met Val Phe Leu Asp Phe Arg Phe
                485                 490                 495

Leu Glu Gln Lys Ile Arg His Asp Ser Thr Ala Trp Asn Ala Ser Gly
            500                 505                 510

Ser Ile Leu Asn Thr Leu Gln Gln Leu Lys Phe Tyr Lys Pro Tyr Ile
        515                 520                 525

Cys Asp Asn Asp Pro Lys Tyr Glu Arg Leu Val Asn Ala Ile Leu Asp
    530                 535                 540

Phe Leu Pro Lys Ile Glu Glu Asn Leu Ile Cys Ser Lys Tyr Thr Asp
545                 550                 555                 560

Leu Leu Arg Ile Ala Leu Met Ala Glu Asp Glu Ala Ile Phe Glu Glu
                565                 570                 575

Ala His Lys Gln Val Gln Arg Phe Asp Asp Arg Val
            580                 585

<210> SEQ ID NO 8
<211> LENGTH: 549
<212> TYPE: PRT
<213> ORGANISM: Caenorhabditis elegans

<400> SEQUENCE: 8

Met Leu Cys Glu Ile Glu Cys Arg Ala Leu Ser Thr Ala His Thr Arg
1               5                   10                  15

Leu Ile His Asp Phe Glu Pro Arg Asp Ala Leu Thr Tyr Leu Glu Gly
            20                  25                  30
```

-continued

```
Lys Asn Ile Phe Thr Glu Asp His Ser Glu Leu Ile Ser Lys Met Ser
            35                  40                  45

Thr Arg Leu Glu Arg Ile Ala Asn Phe Leu Arg Ile Tyr Arg Arg Gln
        50                  55                  60

Ala Ser Glu Leu Gly Pro Leu Ile Asp Phe Phe Asn Tyr Asn Asn Gln
65                  70                  75                  80

Ser His Leu Ala Asp Phe Leu Glu Asp Tyr Ile Asp Phe Ala Ile Asn
                85                  90                  95

Glu Pro Asp Leu Leu Arg Pro Val Val Ile Ala Pro Gln Phe Ser Arg
            100                 105                 110

Gln Met Leu Asp Arg Lys Leu Leu Gly Asn Val Pro Lys Gln Met
        115                 120                 125

Thr Cys Tyr Ile Arg Glu Tyr His Val Asp Arg Val Ile Lys Lys Leu
        130                 135                 140

Asp Glu Met Cys Asp Leu Asp Ser Phe Phe Leu Phe Leu His Gly Arg
145                 150                 155                 160

Ala Gly Ser Gly Lys Ser Val Ile Ala Ser Gln Ala Leu Ser Lys Ser
                165                 170                 175

Asp Gln Leu Ile Gly Ile Asn Tyr Asp Ser Ile Val Trp Leu Lys Asp
            180                 185                 190

Ser Gly Thr Ala Pro Lys Ser Thr Phe Asp Leu Phe Thr Asp Ile Leu
        195                 200                 205

Leu Met Leu Lys Ser Glu Asp Asp Leu Leu Asn Phe Pro Ser Val Glu
        210                 215                 220

His Val Thr Ser Val Val Leu Lys Arg Met Ile Cys Asn Ala Leu Ile
225                 230                 235                 240

Asp Arg Pro Asn Thr Leu Phe Val Phe Asp Asp Val Val Gln Glu Glu
                245                 250                 255

Thr Ile Arg Trp Ala Gln Glu Leu Arg Leu Arg Cys Leu Val Thr Thr
            260                 265                 270

Arg Asp Val Glu Ile Ser Asn Ala Ala Ser Gln Thr Cys Glu Phe Ile
        275                 280                 285

Glu Val Thr Ser Leu Glu Ile Asp Glu Cys Tyr Asp Phe Leu Glu Ala
        290                 295                 300

Tyr Gly Met Pro Met Pro Val Gly Glu Lys Glu Glu Asp Val Leu Asn
305                 310                 315                 320

Lys Thr Ile Glu Leu Ser Ser Gly Asn Pro Ala Thr Leu Met Met Phe
                325                 330                 335

Phe Lys Ser Cys Glu Pro Lys Thr Phe Glu Lys Met Ala Gln Leu Asn
            340                 345                 350

Asn Lys Leu Glu Ser Arg Gly Leu Val Gly Val Glu Cys Ile Thr Pro
        355                 360                 365

Tyr Ser Tyr Lys Ser Leu Ala Met Ala Leu Gln Arg Cys Val Glu Val
        370                 375                 380

Leu Ser Asp Glu Asp Arg Ser Ala Leu Ala Phe Ala Val Met Pro
385                 390                 395                 400

Pro Gly Val Asp Ile Pro Val Lys Leu Trp Ser Cys Val Ile Pro Val
                405                 410                 415

Asp Ile Cys Ser Asn Glu Glu Gln Leu Asp Asp Glu Val Ala Asp
            420                 425                 430

Arg Leu Lys Arg Leu Ser Lys Arg Gly Ala Leu Leu Ser Gly Lys Arg
        435                 440                 445

Met Pro Val Leu Thr Phe Lys Ile Asp His Ile Ile His Met Phe Leu
```

-continued

```
                450                     455                     460
Lys His Val Val Asp Ala Gln Thr Ile Ala Asn Gly Ile Ser Ile Leu
465                     470                     475                     480

Glu Gln Arg Leu Leu Glu Ile Gly Asn Asn Asn Val Ser Val Pro Glu
                485                     490                     495

Arg His Ile Pro Ser His Phe Gln Lys Phe Arg Arg Ser Ser Ala Ser
                500                     505                     510

Glu Met Tyr Pro Lys Thr Thr Glu Glu Thr Val Ile Arg Pro Glu Asp
        515                     520                     525

Phe Pro Lys Phe Met Gln Leu His Gln Lys Phe Tyr Asp Ser Leu Lys
        530                     535                     540

Asn Phe Ala Cys Cys
545
```